United States Patent [19]

Blakely et al.

[11] Patent Number: 5,228,883

[45] Date of Patent: Jul. 20, 1993

[54] PORTABLE DRUG DELIVERY SYSTEM

[75] Inventors: David C. Blakely, Mountain View, Calif.; Dale C. Harris, Fairland, Ind.

[73] Assignee: Eli Lilly and Company, Indianapolis, Ind.

[21] Appl. No.: 695,495

[22] Filed: May 2, 1991

[51] Int. Cl.⁵ .............................................. A61M 5/00
[52] U.S. Cl. ............................... 604/232; 604/235; 604/187; 604/208; 222/327; 222/386
[58] Field of Search ............... 604/187, 218, 232, 233, 604/235, 223, 228, 214, 207, 208, 57, 181; 222/327, 326, 386

[56] References Cited

U.S. PATENT DOCUMENTS

| Re. 32,214 | 7/1986 | Schramm | 604/232 |
|---|---|---|---|
| 1,685,984 | 10/1928 | Cournand et al. | 604/235 |
| 1,757,809 | 5/1930 | Montuori. | |
| 2,074,401 | 3/1937 | Kauzal. | |
| 2,118,221 | 5/1938 | Montuori | 604/235 |
| 2,624,338 | 1/1953 | Moore et al. | 604/223 |
| 2,748,767 | 6/1956 | Wright | 604/232 X |
| 2,966,910 | 1/1961 | Camber | 604/234 X |
| 3,141,583 | 7/1964 | Mapel et al. | 604/234 X |
| 3,469,750 | 9/1969 | Vanderbeck. | |
| 3,744,493 | 7/1973 | Booher et al.. | |
| 3,796,359 | 3/1974 | Dick. | |
| 3,997,085 | 12/1976 | Lindquist | 222/326 |
| 4,033,346 | 7/1977 | Phillips et al.. | |
| 4,255,996 | 3/1981 | Choksi et al. | 83/140 |
| 4,275,628 | 6/1981 | Greenhouse | 83/167 |
| 4,315,448 | 2/1982 | Ball | 83/167 |
| 4,375,849 | 3/1983 | Hanifl | 206/366 |
| 4,472,141 | 9/1984 | Dragan | 604/232 X |
| 4,488,643 | 12/1984 | Pepper | 206/366 |
| 4,520,926 | 6/1985 | Nelson | 206/366 |
| 4,553,687 | 11/1985 | Harkins et al. | 225/93 |
| 4,576,281 | 3/1986 | Kirksey | 206/370 |
| 4,657,139 | 4/1987 | Hanifl | 220/336 |
| 4,667,821 | 5/1987 | Shillington | 206/366 |
| 4,738,664 | 4/1988 | Pringle | 604/228 |
| 4,786,280 | 11/1988 | Maeda | 604/110 |
| 4,968,303 | 11/1990 | Clarke et al. | 604/187 |
| 5,022,563 | 6/1991 | Marchitto et al. | 222/327 |
| 5,098,382 | 3/1992 | Haber et al. | 604/110 |
| 5,167,641 | 12/1992 | Schmitz | 604/196 |

FOREIGN PATENT DOCUMENTS

| 1077384 | 3/1960 | Fed. Rep. of Germany | 604/223 |
|---|---|---|---|
| 1583163 | 10/1969 | France | 603/223 |
| 8701945 | 4/1987 | World Int. Prop. O. | 604/218 |

Primary Examiner—C. Fred Rosenbaum
Assistant Examiner—Mark O. Polutta
Attorney, Agent, or Firm—Robert E. Lee; Leroy Whitaker

[57] ABSTRACT

An improved drug delivery system comprising a gun style injection device used for holding and administering a disposable pre-filled drug cartridge, a holster device used for receiving an end of the gun style injection device and thereafter severing cannula from cartridge and disposing of spent cannulas and cartridges, and an improvement to the drug cartridge is disclosed. The gun style injection device comprises a barrel, a handle, a hinged and spring loaded squeeze lever, and a safety trigger. The holster device comprises a leg protection panel to which a housing is coupled for disposing of spent cartridges. The holster housing is adapted for receiving the barrel of the gun style injection device. The holster housing provides a means for severing the cannula from a used cartridge and disposing of both the cannula and cartridge in separate containers. The cartridge design itself is improved in order to increase the performance of the gun style injection device and the holster cannula severing mechanism.

8 Claims, 18 Drawing Sheets

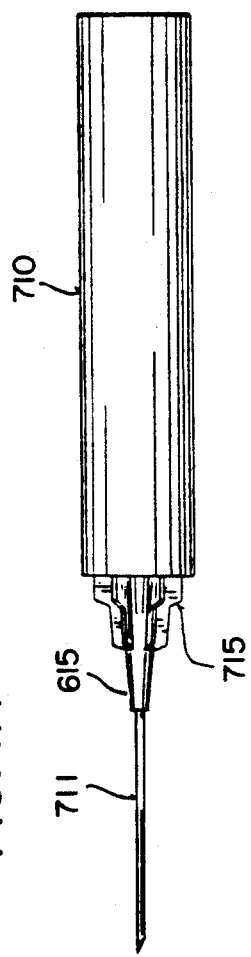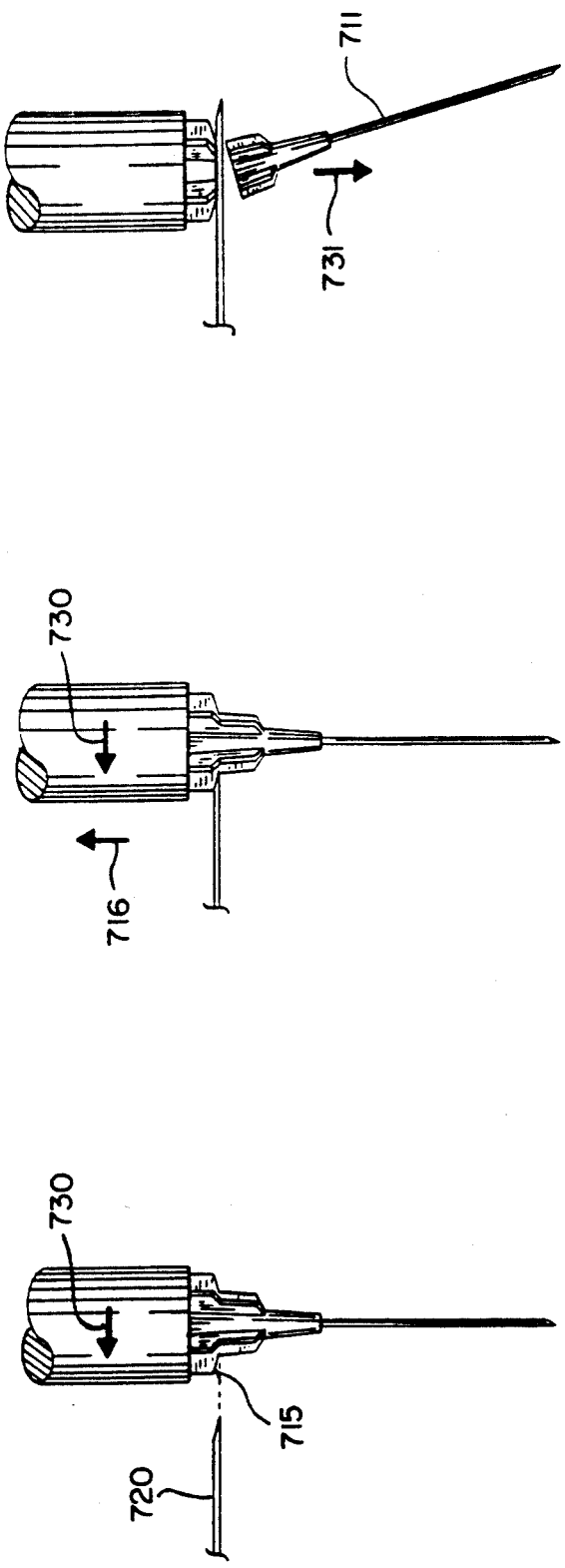
FIG. 7A FIG. 7B FIG. 7C FIG. 7D

PORTABLE DRUG DELIVERY SYSTEM

BACKGROUND OF THE INVENTION

1. Field of the Invention

The present invention relates to portable drug delivery systems. Specifically, the present invention relates to a belt-mounted hypodermic syringe discharge unit with a corresponding belt-mounted holster.

2. Prior Art

Medical personnel are sometimes required to administer subcutaneous injections to patients in the field or outside the confines of a medically sterile and temperature controlled clinical environment. Veterinarians are often called upon to administer injections to domestic livestock in barnyards, corrals, out-buildings, or on the open range. In a domestic livestock operation for example, ranchers or veterinarians are responsible for administering drug formulations to a large herd of livestock on a periodic basis. Such periods between injections may be as short as a few days. In these situations it is imperative that a drug delivery system provide a means for inoculating a large number of animals in a short amount of time. In order to effectively operate in these environments, a drug delivery system must be portable, reliable, convenient, and facilitate the quick administration of drug dosages to as many recipients as possible in minimal time.

In addition to ready portability and ease of use, such systems must be designed to minimize the risk of cross contamination between humans or animals. The typical prior art system uses disposable prefilled drug cartridges with attached cannulas (needles). These disposable cartridges can be prefilled with a variety of liquid formulations including antibiotics, steroids, vitamins, or formulations for increasing milk or meat yield in domestic animals. One particularly significant formulation is bovine somatotropin (BST) for use as an agent for increasing milk production efficiency of dairy cows. While the use of disposable cartridges significantly reduces the problem of cross contamination, several problems exist in the prior art. First, there is a tendency toward excess breakage of cannulas from the cartridges. Excess splitting of the cartridges is also present. These problems arise due to the viscous character of the formulations pre-filled in the cartridges. In order to overcome the formulation viscosity, a great deal of pressure must be applied to the syringe plunger in order to administer the formulation. The fact that some formulations must be refrigerated between the point of manufacture and the point of use exacerbates this problem.

In addition to the fact that some prior art systems using disposable cartridges experience breakage of the cartridge, another problem exists in the disposal of spent (used) cartridges. The sharp cannula attached to each disposable cartridge poses a health and safety hazard not only to animals and humans during the drug administration process, but also a hazard to the general public once the spent cartridges enter the stream of public waste disposal. In addition, some state and federal regulations require that spent drug cartridges be destroyed in order to prevent re-use of the cartridge. It is also advantageous to separate the metallic cannula from the typically plastic disposable cartridge in order that the two components of different characteristics may be disposed of separately. Prior art drug delivery systems typically do not provide a means for conveniently and safely removing the cannula from the spent disposable cartridge. Further, prior art systems typically do not provide a means for disposing of the cannula separate from the spent cartridge.

Prior art drug delivery systems experiencing breakage of disposable cartridges, or not providing ready means for destroying and disposing spent cartridges, cannot satisfy the requirements for an efficient and effective drug delivery system. Thus, an improved drug delivery system is needed.

SUMMARY OF THE INVENTION

The present invention provides an improved drug delivery system comprising two basic components. First, a gun style injection device used for holding and administering a disposable pre-filled drug cartridge is disclosed. Secondly, a holster device used for receiving an end of the gun style injection device and thereafter severing cannula from cartridge and disposing of spent cannulas and cartridges is disclosed. In addition, an improvement to the cartridge and the injection device is disclosed.

The gun style injection device of the present invention comprises a barrel, a handle, a hinged and spring loaded squeeze lever, and a safety trigger. The barrel, having a cylindrical bore, is open on one side and adapted for receiving a disposable cartridge with attached cannula inserted cannula end first into a guide at the end of the barrel. The guide serves to hold the disposable cartridge in place and to limit axial movement of the cartridge within the barrel. Within the cylindrical bore of the open side of the barrel is a hinged and spring-loaded ejection plate for forcibly ejecting a spent cartridge from the barrel. The barrel housing also contains a slide lock or cartridge ejection release means for holding the ejection plate in place when the drug in the cartridge is being administered. The cartridge ejection release means also provides a means for releasing the cartridge thereby allowing it to be forcibly ejected from the barrel. A push rod slideably mounted within the cylindrical bore of the barrel and used for administering the drug within the cartridge is operated from a retracted position while the drug cartridge is being loaded to an extended position, where one end of the push rod serves to force a plunger down the extent of the drug cartridge, thereby forcing the drug within to be expelled through the cannula. The other end of the push rod is slideably mounted on the squeeze lever. The push rod also contains a small notch for receiving a stop tab member attached to the safety trigger. The stop tab serves to restrict movement of the push rod down the barrel while the safety trigger is engaged.

The holster device of the present invention comprises a leg protection panel to which a housing is coupled for disposing of spent cartridges. The leg protection panel is comprised of at least three separate plastic sections, connected by flexible metal sheets. The leg protection panel is covered with a weather-proof plastic and formed in a convex shape. The protection panel serves to prevent a user of the system from inadvertently puncturing the user's leg while using the drug delivery system. The convex shape of the panel increases the panel's support strength and serves to better fit the rounded leg of a user of the system. The leg protection panel is further divided into at least three separate sections thereby providing better longitudinal flexibility. On one side of the protection panel are affixed two belt loops and a leg strap allowing the holster to be hung from the waist belt of a user. On the other side of the protection panel, a support strap and snap is provided for holding the gun style injection device while not being used.

Coupled to a lower end of the leg protection panel is a housing adapted for receiving the barrel of the gun style injection device. This housing supports a means for severing the cannula from a used cartridge and disposing of both the cannula and cartridge in separate containers. The holster device further comprises a rotatable receptacle for receiving an end of the injection device, a sharps container slidably mounted to the housing, the sharps container including a cannula (needle) severing means, a means for supporting a spent cartridge containment bag, and a toggle switch for reversing the operable direction of the rotatable receptacle. The rotatable receptacle comprises means for receiving the barrel of the gun style injection device. The receptacle rotates within a cylinder portion of the housing such that the gun style injection device may be inserted into the receptacle and rotated in either direction. As the gun style injection device is rotated a first angular portion within the receptacle, the cartridge located in the gun style injection device is forced into a blade edge fixedly mounted on the sharps container which is installed within the housing thereby causing the severance of the cannula from the cartridge. The severed cannula thereafter drops straight through the receptacle and cylinder portion into the sharps container located directly beneath the receptacle and cylinder portion. As the gun style injection device is rotated a second angular portion, a wedge member fixedly mounted on said housing is brought into contact with the cartridge ejection release means on the gun style injection device thereby causing the ejection of the severed cartridge through an opening in the side of the cylinder portion of the housing into a spent cartridge containment bag supported by said housing. The gun style injection device is subsequently rotated to its original orientation and removed from the receptacle means. The sharps container is slideably mounted on one end of the cylinder portion with a locking mechanism included for locking the sharps container into position. When released, the sharps container can be removed from the housing and sealed using a hinged cover with locking mechanism coupled to the container.

The housing further contains a support ridge around said housing for holding and supporting a spent cartridge containment bag. The housing also contains two rounded guide panels coupled to the housing for guiding and shaping the spent cartridge containment bag. The guide panels also protect the containment bag from being damaged by ejected cartridges.

The cartridge design itself is improved in the present invention in order to increase the performance of the gun style injection device and the holster cannula severing mechanism. A ridge is added to the cartridge cylinder at the end joining the cannula. This ridge is adapted to engage an indentation in the injection device ejection plate thereby locking the cannula end of the cartridge solidly in place for more efficient cutting by the holster severing mechanism. In addition, ribs connecting the cannula to the cartridge cylinder and supporting the cannula are modified to add a wedging surface adapted to properly align and position the holster severing blade for more accurate cutting.

Two additional improvements to the injection device are also described. First, an improvement to the injection device providing a means for adjusting the dosage of drug delivered by the system. A set of longitudinal grooves in the push rod of the injection device cooperate with a tooth in a dosing knob thereby restricting the movement of the push rod in one of four different positions. The dosing knob may be rotated to select the desired length of travel of the push rod.

A second improvement to the ejection plate of the injection device provides a means for allowing cartridge rotation in one direction but limiting rotation in the other direction. An angled tooth extending through an opening in the ejection plate serves to restrict rotation of a loaded cartridge in one direction while allowing rotation in the opposite direction.

BRIEF DESCRIPTION OF THE DRAWINGS

FIGS. 7A–D illustrate a further improvement to the cartridge.

DETAILED DESCRIPTION OF THE PREFERRED EMBODIMENT

Figure 1:
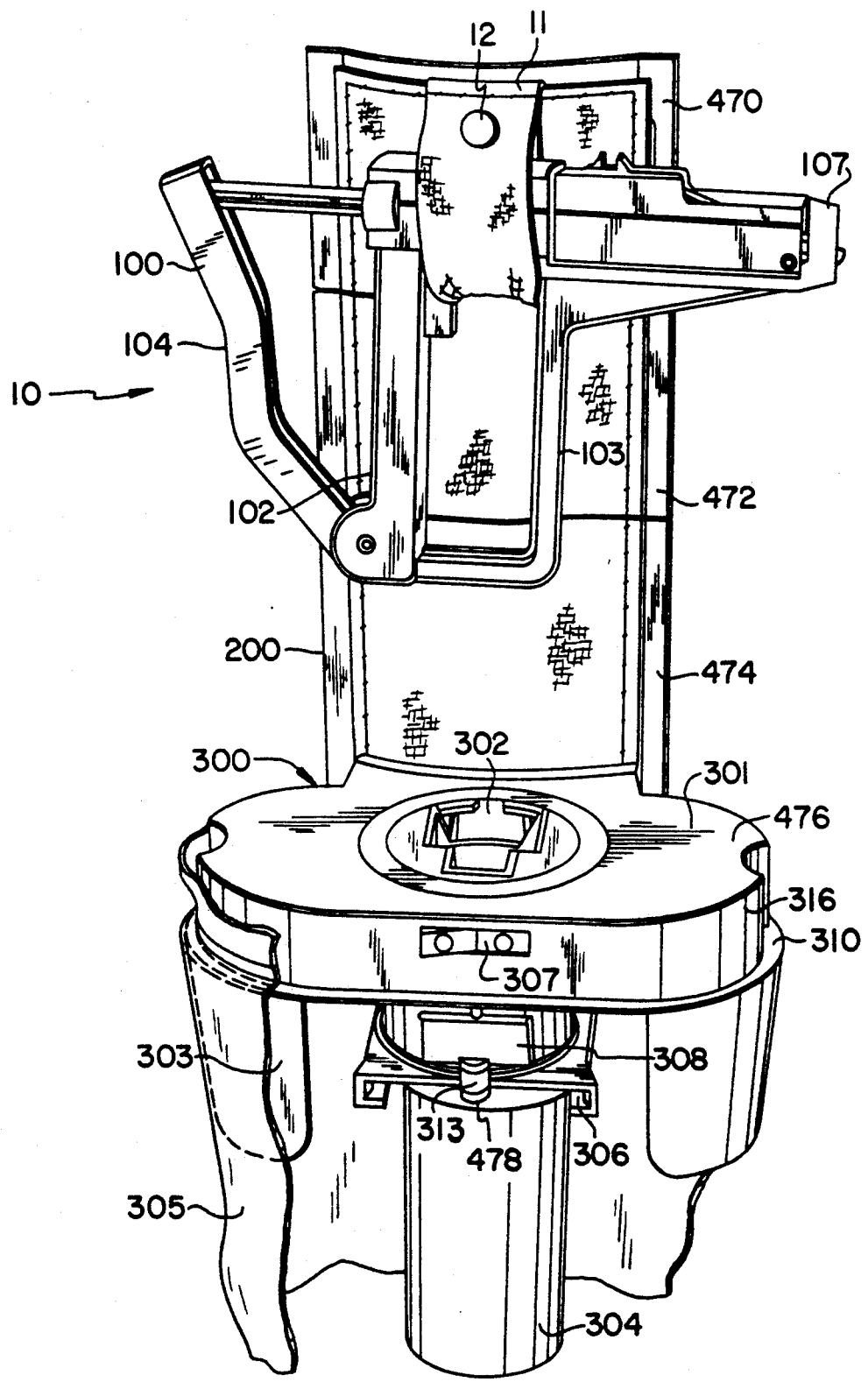
FIG. 1 is a view showing the holster and gun injection system.

In the preferred embodiment, described and illustrated in the drawings provided herein, the present invention provides a readily portable, safe, and efficient drug delivery system comprising a gun style injection device, a holster device for severing and disposing of spent drug cartridges, and an improved drug cartridge. In the following description, for purposes of explanation and not limitation, specific mechanical structures, connections, operation, etc. are set forth in order to provide a thorough understanding of the present invention. However, it will be apparent to one skilled in the art that the present invention may be practiced in other equivalent embodiments that depart from these specific details. In other instances, detailed descriptions of well-known aspects of prior art systems are omitted so as to not obscure the description of the present invention with unnecessary detail.

Referring to FIG. 1, a preferred embodiment of the portable drug delivery system of the present invention designated generally 10 is illustrated. The drug delivery system 10 is shown to comprise a gun style injection device designated generally 100, a holster including a leg protection panel designated generally 200 and a housing and cartridge disposal device designated generally 300. Injection device 100 is shown removably coupled to protection panel 200 by a support strap 11. Support strap 11 is locked into place with a snap 12. When snap 12 is unsnapped, injection device 100 may be removed from protection panel 200. On the other hand, housing and disposal device 300 is permanently coupled to protection panel 200 at a lower end. On the reverse side of protection panel 200, two belt loops are affixed thereto for the purpose of supporting the protection panel 200 and housing and disposal device 300 from the waist belt of a user of the system. Also affixed to protection panel 200, a leg strap 398 (FIG. 3) is provided to securely attach the protection panel 200 to the leg of the user.

Figure 2:
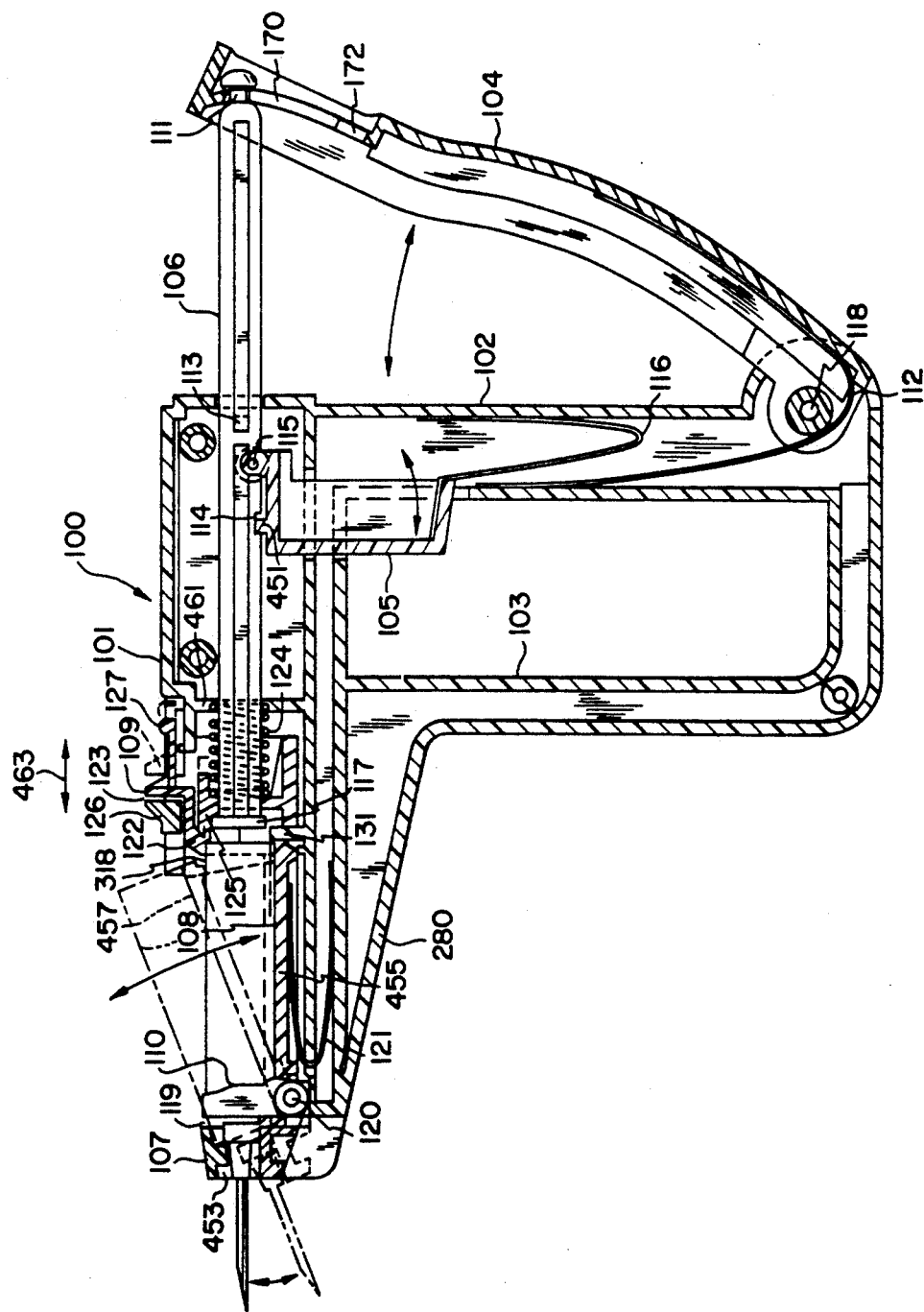
FIG. 2 is a side cut away view of the gun style injection device.
Figure 12:
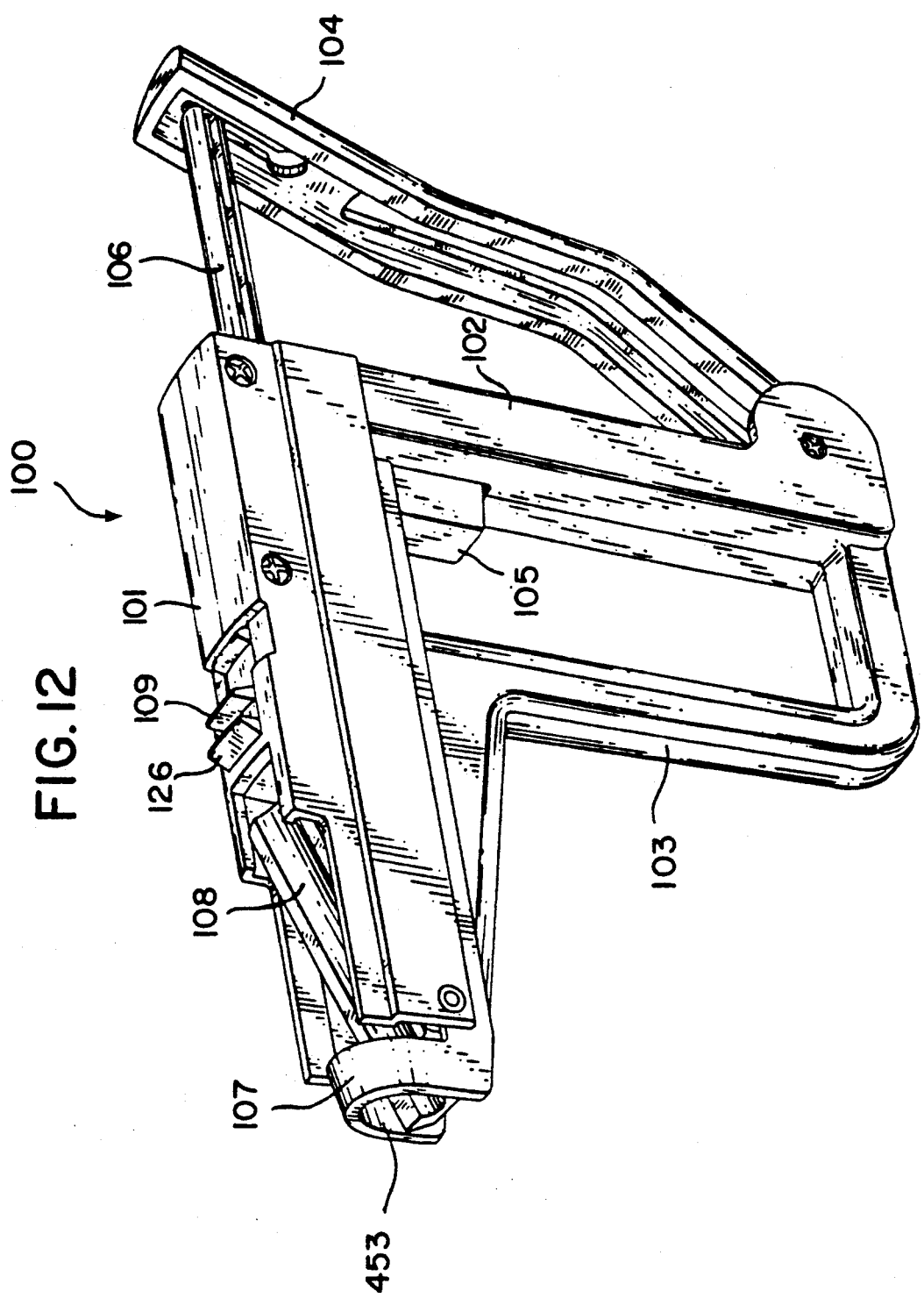
FIG. 12 is a side perspective view of the gun style injection device.

Referring now to FIGS. 2 and 12, the gun style injection device 100 is depicted. As shown, injection device 100 comprises a barrel designated generally 101 coupled to a handle 102 to which a hand guard 103 is coupled. Similarly coupled to handle 102 is a hinged lever 104 which is spring loaded by spring 112. Barrel 101 further comprises a cylindrical bore within which a push rod 106 is slideably disposed. Barrel 101 further comprises a cartridge chamber 110 adapted for receiving and positioning a cartridge coaxial with the bore of barrel 101. Push rod 106 is slideably coupled to said hinged lever 104 at narrowed region 111. Region 111 is actually a ball-in-track joint. The track 170 on hinged lever 104 allows the ball end of the push rod 106 coupled thereto to travel down the track as the hinged lever 104 is squeezed. Hinged lever 104 moves push rod 106 between two positions: an extended position and a relaxed position. As hinged lever 104 is moved (squeezed) towards handle 102, push rod 106 is forced through the cylindrical bore of barrel 101 and into a cartridge positioned within cartridge chamber 110. This action serves to force the contents of the cartridge through the cannula and into a recipient of the injection. In this case, the hinged lever 104 and push rod 106 are in the extended position. As pressure is released on hinged lever 104, spring 112 urges hinged lever 104 to the relaxed position shown in FIG. 2. The return of hinged lever 104 to its relaxed position causes a corresponding retraction of push rod 106 from cartridge chamber 110 through the bore of barrel 101. A stop tab 113 prevents push rod 106 from being fully retracted from the bore of barrel 101. Push rod 106 also contains a notch 114 for receiving a corresponding trigger tab 451 coupled to safety trigger 105. With the trigger tab 451 of safety trigger 105 positioned within notch 114 as shown in FIG. 2, push rod 106 is prevented from moving within the bore of barrel 101, and correspondingly, hinged lever 104 is prevented from moving towards handle 102. This safety mechanism prevents the inadvertent discharge of the contents of a drug cartridge. As safety trigger 105 is depressed towards handle 102 into a release position, safety trigger 105 pivots about hinge 115 thereby causing the trigger tab 451 to be retracted from notch 114. This action causes push rod 106 to be freely moveable within the bore of barrel 101. As safety trigger 105 is released, spring 116 urges safety trigger 105 back into the relaxed position shown in FIG. 2. When is relaxed position, safety trigger 105 again positions trigger tab 451 within notch 114 thereby preventing movement of push rod 106. In an alternative embodiment, spring 112 and spring 116 may be combined into a single spring wherein one end of the spring provides the force necessary for the hinged lever 104, and the other end of the spring provides the force necessary for the safety trigger 105. Hand guard 103 is positioned in proximity to handle 102 in order to protect the hand of a user while the injection device 100 is being operated.

Figure 14:
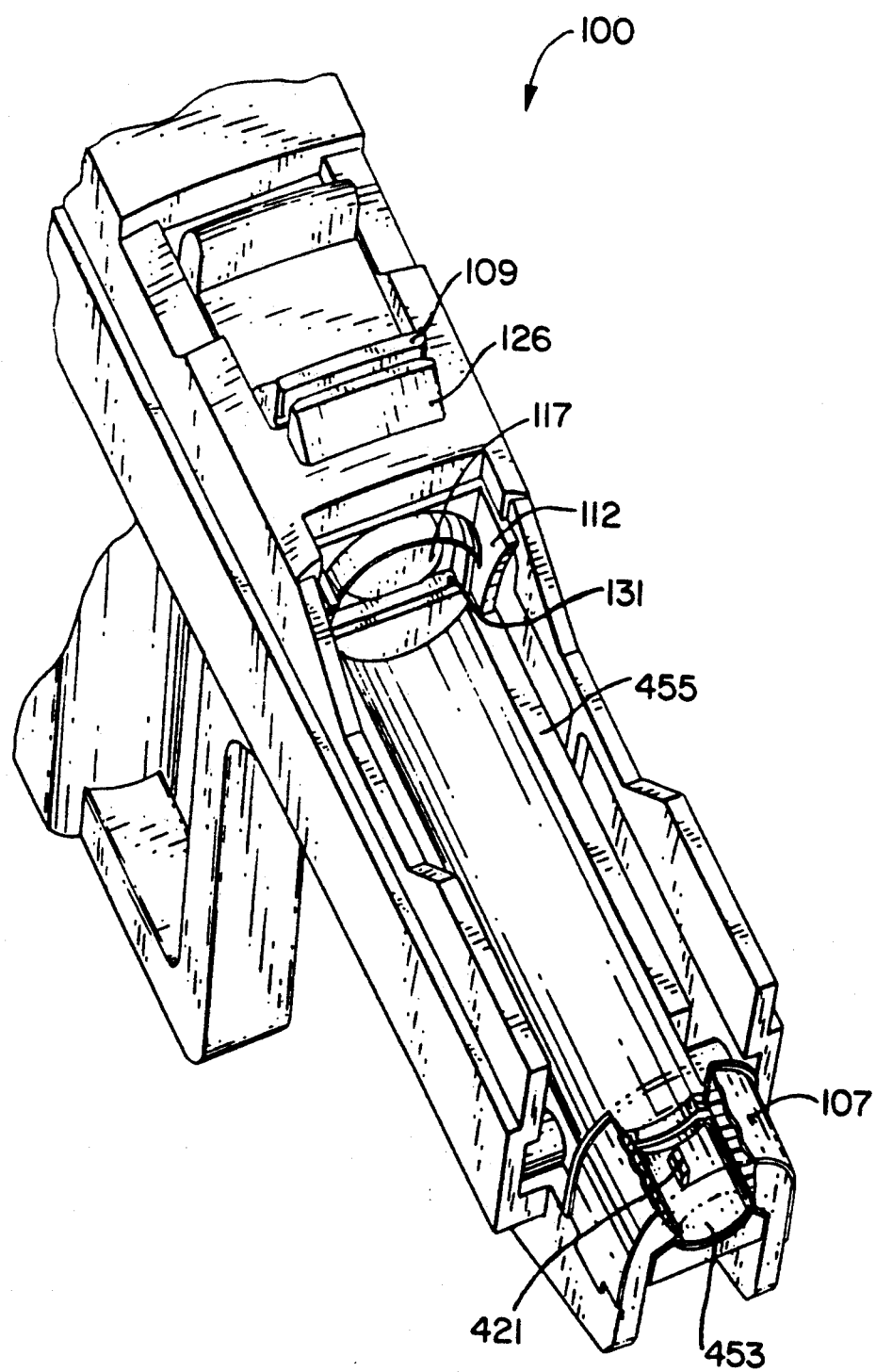
FIG. 14 is a top perspective view of the injection device showing the cartridge chamber.

The forword end of push rod 106 closest to cartridge chamber 110 is terminated by a head 117 which is larger than the shaft of push rod 106 and larger than the bore of barrel 101, as shown in FIG. 12. This head 117 has a diameter slightly smaller than the inside diameter of a cartridge placed in cartridge chamber 110. A flat portion of head 117 (see FIG. 14) assures that head 117 clears cartridge stop 131. Thus, head 117 retracts to a position behind stop 131. The back end of push rod 106, fastened to hinge lever 104 with a ball-in-track joint, has a reduced diameter at 111 in order to be slideably coupled with hinged lever 104 through a key hole slot 172 at the bottom of track 170. The bottom of hinged lever 104 is attached at hinge 118 to handle 102 thereby allowing rotation of hinged lever 104 about the center of hinge 118. The back surface of hinged lever 104 is curved to fit the palm of a hand. At the foreword end of barrel 101, a cartridge guide 107 is coupled to the barrel 101. The cartridge guide 107 contains an aperture 453 adapted for receiving the cannula end of a drug cartridge with a sheath over the cannula. Aperture 453 forms a cylindrical opening with an interior dimension slightly larger than the cannula end of a drug cartridge. As a cartridge is inserted into cartridge guide 107 and depressed into an operating position within chamber 110, the cannula end of the cartridge is, at the same time, raised to meet the interior upper surface of cartridge guide 107. This action serves to properly position the cannula end of a drug cartridge within chamber 110. Cartridge guide 107 also serves to properly position a cartridge relative to slot 119. The cannula is severed from the cartridge through slot 119. A holster device, described below, includes a cutting blade element which is specially adapted and positioned to pass through slot 119 thereby severing the cannula from the cartridge. Cartridge guide 107 facilitates this process by rigidly holding the cartridge and cannula in place while the severing operation occurs.

An important element of injection device 100 is ejection means 108. Ejection means 108 provides a means for forcibly removing a spent cartridge with a severed cannula from chamber 110. Ejection means designated generally 108 comprises an ejection plate 455 of a dimension to fit within chamber 110. Ejection means 108 is coupled to barrel 101 at hinge 120. Thus coupled, ejection means 108 is free to rotate about the center of hinge 120. This rotation of ejection means 108 occurs between a cartridge loading position shown in phantom, where one end 457 of said ejection plate 455 extends out of said chamber such that a new cartridge may be loaded into chamber 110, and an operating position, where both ends of said ejection plate 455 are positioned within said chamber and a cartridge resting on said ejection plate 455 is positioned coaxial with the bore of barrel 101. A spring 121, positioned underneath ejection means 108 as shown, serves to urge ejection means 108 in the upward direction thereby forcibly removing a spent cartridge from chamber 110 when the ejection means is not locked in place by ejection release means 109. Once a spent cartridge has been ejected from chamber 110 by ejection means 108, ejection means 108 is in the loading position and ready for the insertion of a new cartridge. When the new cartridge is placed into position on the plate of ejection means 108 and pushed down into the operating position, the plate of ejection means 108 serves to properly align the cartridge in coaxial configuration with the bore of barrel 101.

A cartridge is locked into an operating position coaxial with the bore of barrel 101 using an ejection release means 109. Ejection release means 109 is slideably mounted on barrel 101 along push rod 106. Ejection release means 109 is configured to slide in a direction parallel to the movement of push rod 106 within the bore of barrel 101. The movement of ejection release means 109 operates between two positions: a cartridge lock position and a cartridge release position. In the cartridge lock position, a front edge 122 of ejection release means 109 makes contact with an upper surface of ejection means 108. In addition, edge 122 makes contact with a cartridge loaded in chamber 110 and holds the cartridge 318 down in the operating position. Spring 124, compressed between an intermediate wall 461 within barrel 101 and circumferential tab 125 of release means 109, serves to urge ejection release means 109 into the cartridge lock position by applying pressure to circumferential tab 125. In the cartridge lock position, ejection release means 109 overcomes the force being applied by spring 121 to the underneath side of ejection means 108. A cartridge positioned in chamber 110 is thereby held in an operating position (i.e. coaxial with the bore of barrel 101) by release means 109. Ejection release means 109 is moved to the cartridge release position by sliding ejection release means 109 backwards in a direction away from chamber 110. This action is depicted in FIG. 2 by the line and arrows 463 and with a portion of ejection release means 109 shown in phantom. As ejection release means 109 is moved to the cartridge release position, locking edge 122 is moved away from and ceases to make further contact with a cartridge 318 in chamber 110. Once a cartridge is free of locking edge 122, spring 121 is then free to force ejection means 108 in the upward direction thereby forcibly removing the cartridge from chamber 110. The leading surface of locking edge 122 is angled such that a cartridge may be depressed into the operating position without directly manipulating ejection release means 109. The wedge action of the leading surface of locking edge 122 serves to temporarily displace ejection release 109 into the cartridge release position while a cartridge is snapped into the operating position. Spring 124 then operates to urge the ejection release 109 back into the lock position thereby locking the cartridge into an operating position within chamber 110. The push rod 106 passes through the aperture formed by circumferential tab 125 helping to capture the ejection release means 109 to the barrel 101.

An ejection support means 126 is fixedly attached to the upper side of barrel 101. Ejection support means 126 serves to define a slot 123 between a surface of ejection support means 126 and a surface of ejection release means 109. Slot 123 is particularly adapted for automatically activating ejection release 109 by a wedge member affixed to the holster device as described below. The holster wedge member is positioned for insertion into slot 123 when injection device 100 is rotated in the holster device as described below. As the holster wedge member is inserted into slot 123, ejection release means 109 is forced backward into the cartridge release position thereby causing the ejection of a spent cartridge from chamber 110. Ejection support means 126 serves to assist the holster wedge member in forcing release switch 109 to the cartridge release position. Ejection release 109 is also provided with a small rounded end 127 for manual operation of the switch. By activation of ejection release means 109 either automatically using a holster wedge member or manually using rounded end 127, ejection release means 109 requires a force applied to move ejection release means 109 into the cartridge release position thereby allowing a cartridge to be ejected from chamber 110. When this force is released, ejection release means 109 is returned to the cartridge lock position by virtue of the force applied by spring 124.

With the exception of the spring components of the gun style injection device 100, the entire device may be manufactured of a plastic material. For example, the injection device 100 may be molded of a polypropylene or polycarbonate material. Techniques for molding plastic in this fashion are well know to those skilled in the art. The overall structural and reinforcing members of the injection device 100 are as shown in the accompanying drawings. Thus, the gun style injection device 100 of the present invention is described.

Referring again to FIG. 1, the protective panel 200 and holster device 300 are shown. The leg protection panel 200 is comprised of at least three separate plastic sections, connected by flexible metal sheets. The leg protection panel 200 is covered with a weather proof plastic and formed in a convex shape. The protection panel 200 serves to prevent a user of the system from inadvertently puncturing the user's leg while using the drug delivery system. The convex shape of the panel 200 increases the panel's support strength and serves to better fit the rounded leg of a user of the system. The leg protection panel 200 is further divided into at least three separate but coupled sections even numbers 470 through 474 thereby providing better longitudinal flexibility. On one side of the protection panel 200 are affixed two belt loops allowing the holster 300 to be hung from the waist belt of a user. On the other side of the protection panel, a support strap 11 and snap 12 is provided for holding the gun style injection device while not being used. Also affixed to protection panel 200, a thigh strap 398 is provided to securely attach the protection panel 200 to the leg of the user.

Figure 3:
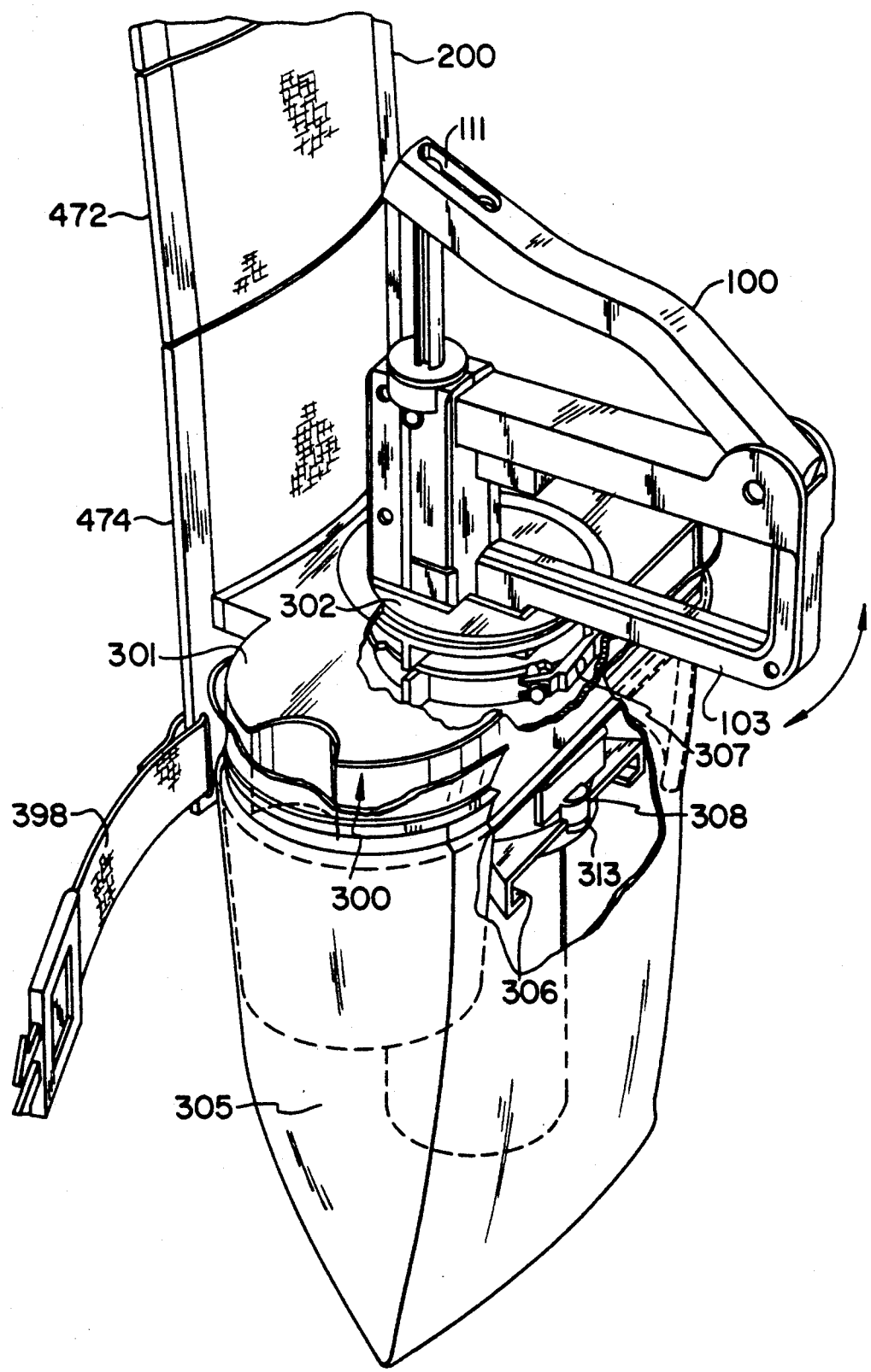
FIG. 3 is a side perspective view of the holster with the gun style injection device inserted in the receptacle of the holster, a portion of the Figure shown broken away.
Figure 15:
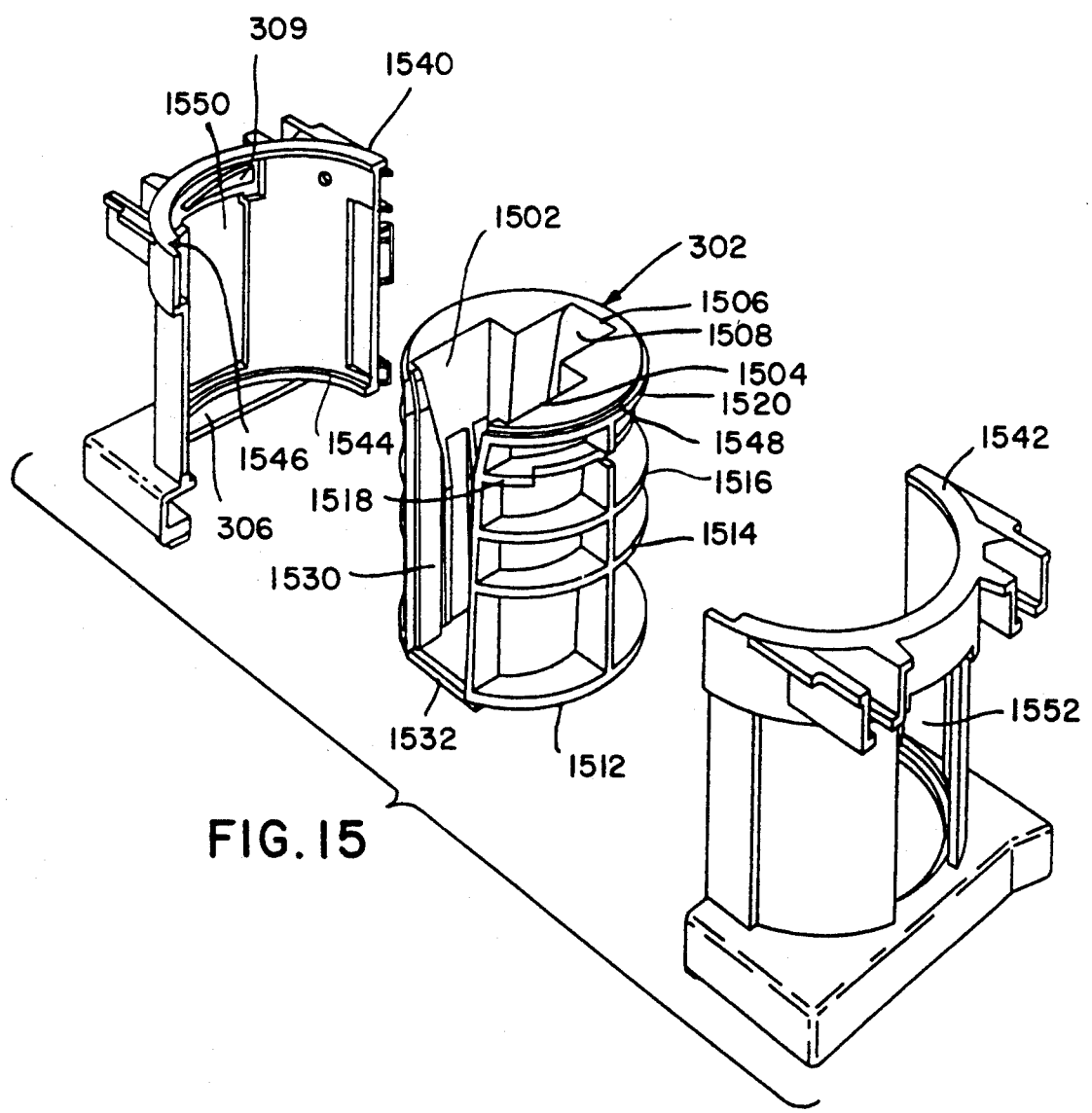
FIG. 15 is an exploded perspective view of the rotated receptable and cylindrical portions of the holster of the system of FIG. 1.

Holster 300 is shown to comprise a housing 301 affixed to leg protection panel 200 at a lower end of section 474. Housing 301 includes a flat upper surface 476 in the center of which a recessed, rotatable, gun receptacle 302 is positioned. Referring now to FIG. 15 for more details on the rotatable gun receptacle 302 is generally cylindrical in shape and is a molded part from plastic in the preferred embodiment. A channel comprising a plurality of rectangular portions shaped to receive the cartridge containing end of the gun passes through the center of the cylinder. The combination rectangular channel comprises two opposing side surfaces 1502 and 1504 separated by a third rectangular surface 1506 which includes a slanted interior bottom 1508 which supports the angled frame 280 shown in FIG. 2. The cartridge-containing end of the gun will slide easily into the multirectangular channel of the receptacle 302 until the outside surface of the handle guard 103 engages the flat surface of the housing 301 of the holster. This is shown in FIG. 3.

The cylindrical shape of the receptacle 302 is formed by a number of parallel and spaced-apart annular surfaces even numbers of 1512 through 1520. Annular surface 1520 is the top surface in which the rectangularly shaped channel is formed and surface 1512 is the bottom surface of the cylinder. These annular surfaces are really rib like in structure and provide support for the receptacle 302 without adding a large amount of mass and adding weight to the holster. The rectangular channel opens up to ambient atmosphere through a rectangular opening 1530 in a side of the receptacle 302. The opening 1530 extends from the bottom surface 1512 to the top annular surface 1520 except for a straight bridge member 1532 attached to the bottom of the plate 1512 across the opening.

The receptacle 302 is attached to the housing 301 by a receptacle housing which is shown in FIG. 15 separated into two halves 1540 and 1542. To assemble the receptacle and the receptacle housing with the housing 301, the two halves 1540 and 1542 are brought together to encircle the receptacle 302. The bottom annular surface 1512 is captured by an annular ridge 1544 in the bottom of halves 1540 and 1542 which forms a completed circle when the two halves 1540 and 1542 are brought together. Similarly, annular ledge 1546 mates with an annular channel 1548 on the top plate 1520 of the receptacle 302. Hence, when the two halves of the receptacle housing 1540 and 1542 are brought together to encircle the cylinder 302, the cylinder 302 becomes captured between the bottom circular ridge 1544 and the top circular ledge 1546 of the receptacle housing formed from halves 1540 and 1542. The receptacle housing halves 1540 and 1542 are adapted to be bolted to the bottom surface of the housing 301. In so doing, the top surface of plate 1520 of the receptacle 302 becomes coplaner with the surface 476 of the housing.

Each of the housing halves 1540 and 1542 have a side rectangular opening 1550 and 1552, respectively. The receptacle 302 is able to rotate within the receptacle housing and the opening 1530 can be aligned with either the opening 1550 or 1552.

Housing 301 further includes a side panel 316 coupled to said upper surface of housing 301. A support rim 310 extending from said side panel 316 and extending entirely around housing 301 provides a means for supporting a cartridge disposal bag 305 used for containing spent drug cartridges with cannulas having been severed therefrom. The open end of cartridge disposal bag 305 is large enough to slide over the top of support rim 310 yet small enough to rest firmly on support rim 310 without falling off. Housing 301 further includes guide plates 303 attached to said side panels 316 and extending downwardly therefrom; said guide plates 303 for guiding cartridge disposal bags 305 over rim 310 and for properly shaping cartridge disposal bag 305. The inner surface of guide plates 303 further provide the benefit of protecting cartridge disposal bag 305 from damage by cartridges being ejected from within gun receptacle 302.

Figure 16A:
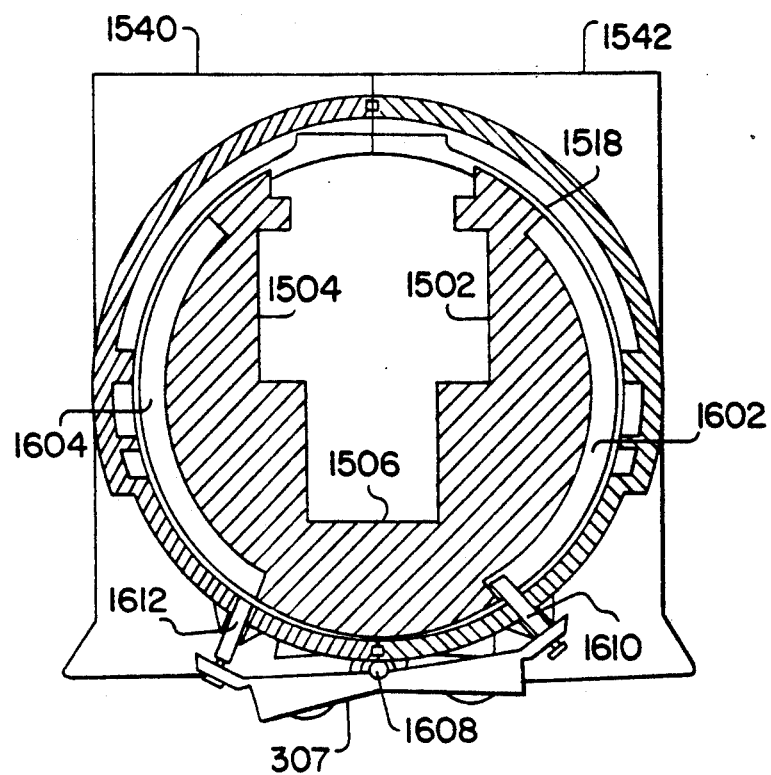
FIGS. 16A and 16B are top cross sectional views of the assembled receptacle and cylindrical portions of FIG. 15 taken through a plane depicting the selection of the direction of rotation of the rotational receptacle.
Figure 16B:
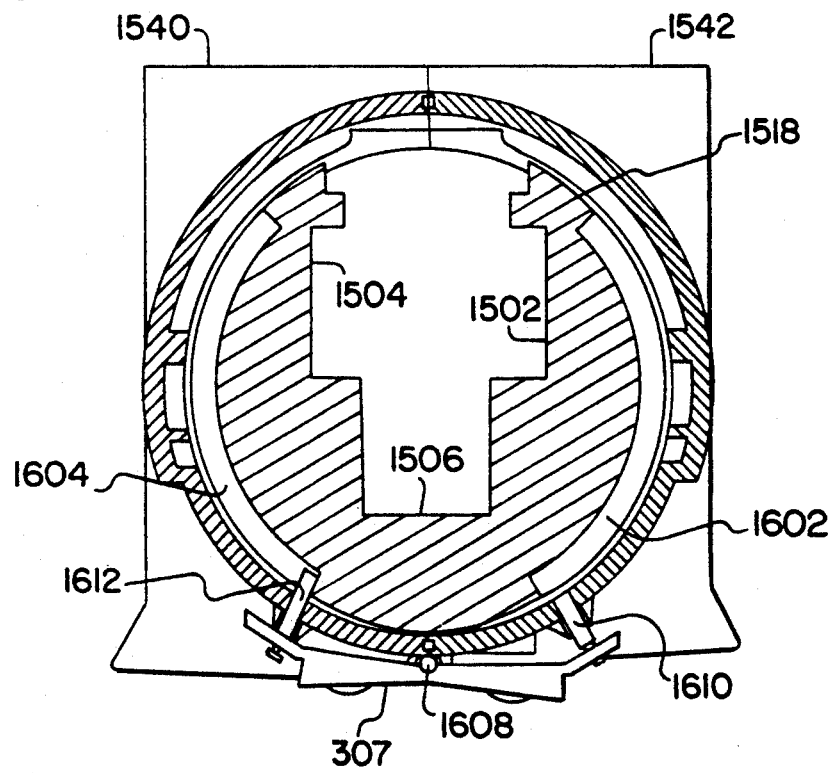

Referring now to FIGS. 16A and B, a top cross sectional view of the receptacle 302 assembled together with the receptacle housing halves 1540 and 1542 through the plane containing the annular surface 1518 is shown. The circular outer perimeter of the surface 1518 contains two 90° cut outs or slots 1602 and 1604. The slots are located on either side of the rectangularly shaped channel in the center of the receptacle 302.

A rotation direction select switch 307 is attached to the housing halves 1540 and 1542 about a pivot point 1608 and extends through an opening in side panel 316. Rotation direction select switch 307 serves to select the rotation direction of cylinder 302. Rotation direction select switch 307 provides a selection between one of two directions of movement: clockwise or counter clockwise movement of rotatable cylinder 302. By depressing one side of rotation direction select switch 307, a pin (1610 or 1612) is extended into slot 1602 or 1604, respectfully, thereby restricting movement in one of two directions. Because the slot is 90°, the receptacle can rotate 90°.

The lower ends of receptacle housing halves 1540 and 1542 form a sharps container slide mount 306 when they are attached together. Sharps container slide mount 306 is particularly adapted to receive and support the upper rim 902 on upper opposite sides of sharps container 304. Thus, sharps container 304 may be slid free and removed from holster 300.

Figure 9A:
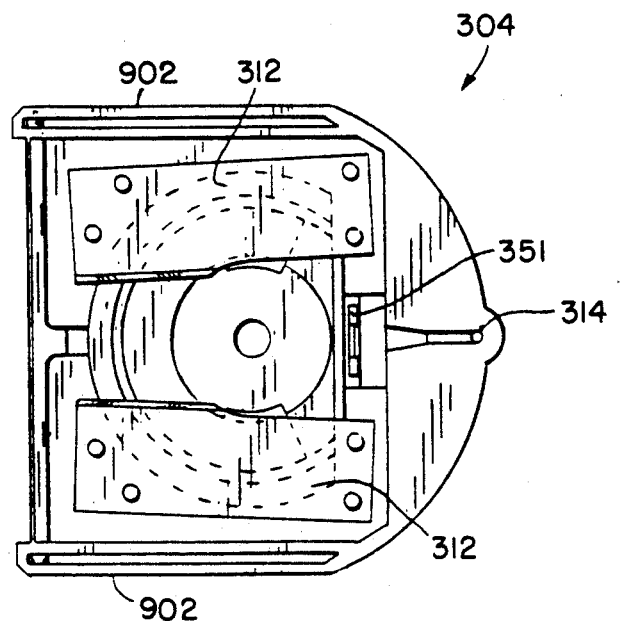
FIG. 9A is a top planer view of the sharps container of the holster portion of holster and gun injection system of FIG. 1.

Sharps container 304 is designed to hold a collection of spent and contaminated cannulas that have been severed from used drug cartridges. Sharps container 304 is illustrated in detail in FIGS. 9A through 9C. As shown, a set of blades 312 (i.e. cannula severing means) are attached to the sharps container 304. Sharps container 304 is manufactured of a material suitable to prevent sharp cannulas from piercing the container from within. A sturdy polystyrene or polypropylene material of a suitable thickness may be used for this purpose. Sharps container 304 may be slid into sharps container slide mount 306 and locked into place with sharps container lock 313 attached to slide mount 306 at the opening. See FIG. 1. A pin 478, attached to sharps container lock switch 308, is designed to extend downwardly into an opening 314 (FIG. 9B) in the sharps container thereby locking the sharps container into slide mount 306. When removal of sharps container 304 is necessary, sharps container lock switch 308 is moved in an upward direction thereby removing the lock pin 478 from opening 314 and freeing sharps container 304 for movement out of slide mount 306. A leaf spring (not shown) is inserted at point 315 (FIG. 5) between the sharps container 304 and the end of slide mount 306. The leaf spring urges sharps container 304 out of slide mount 306 when lock pin 478 is removed from lock 313.

Figure 5:
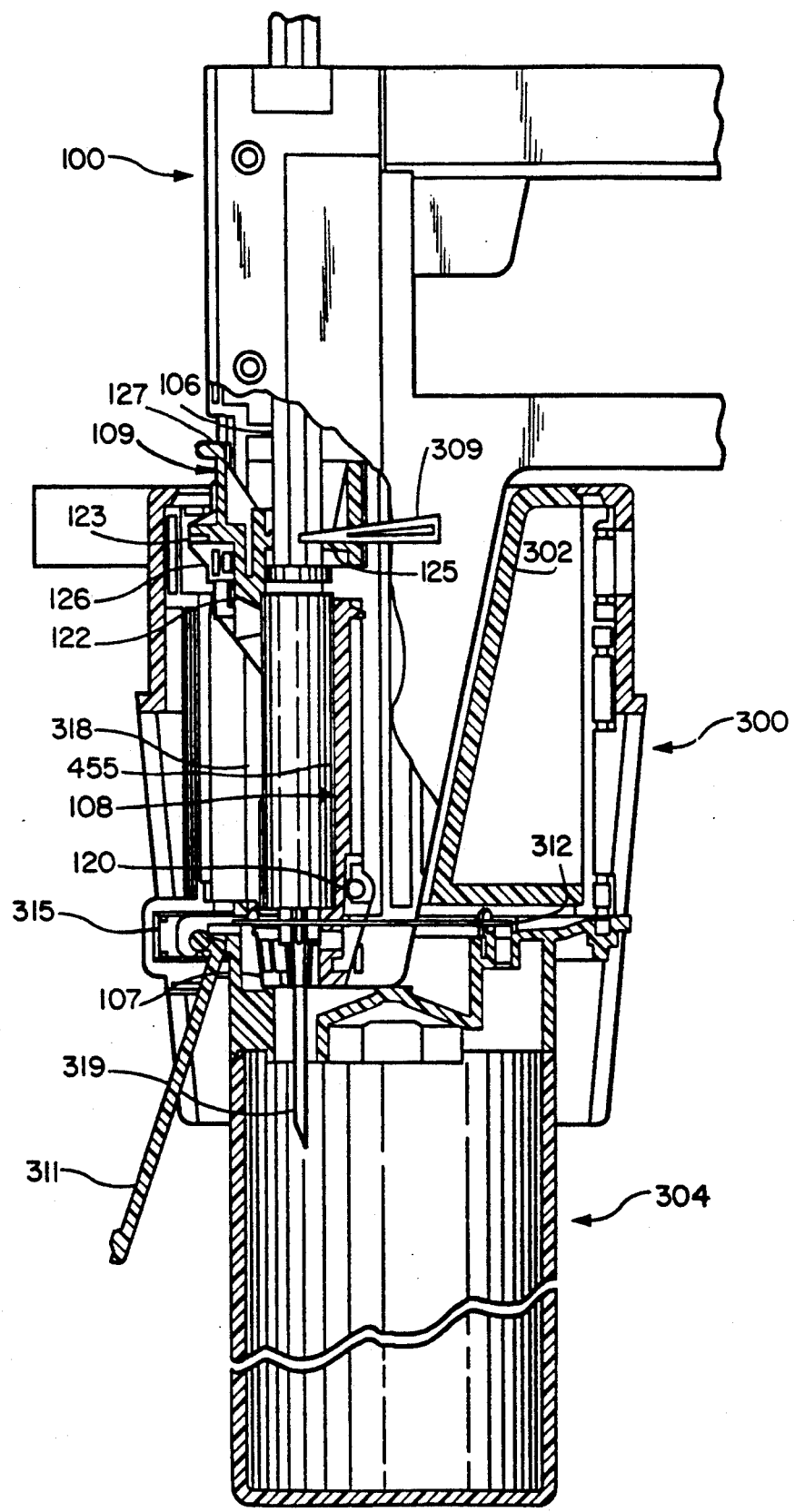
FIG. 5 is a side cut away view of the holster and style injection device showing the severing of the cannula from the spent drug cartridge.
Figure 9B:
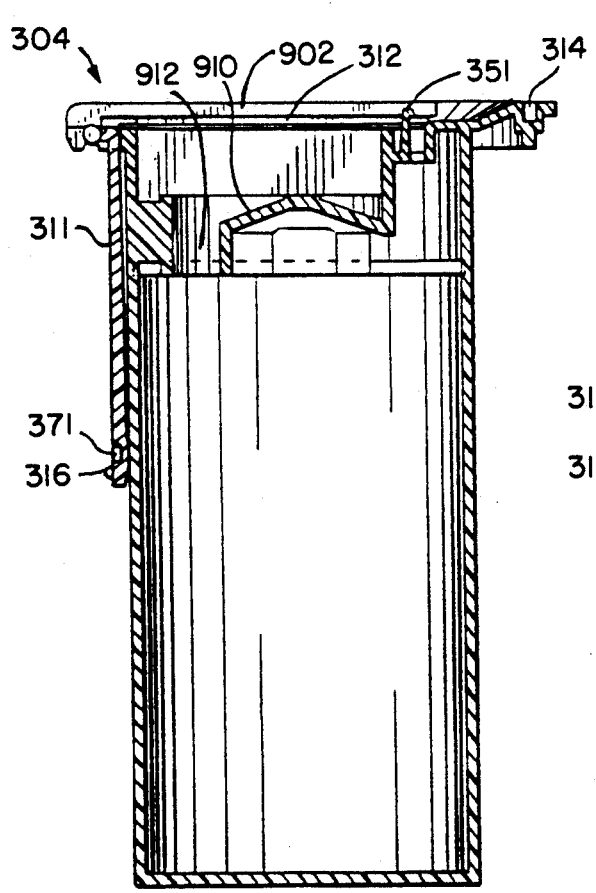
FIG. 9B is a cross sectional view of the elevational planer view of the sharps container of FIG. 9C.
Figure 9C:
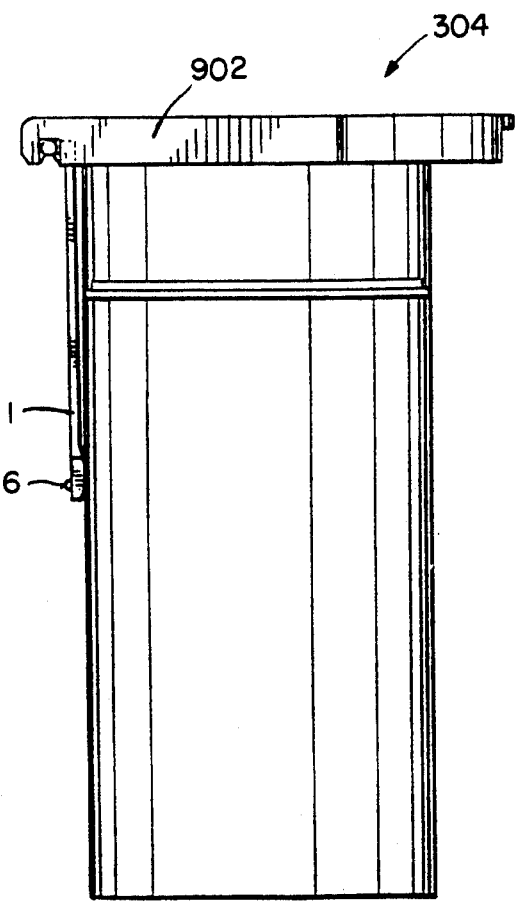

As depicted in FIG. 5 and FIGS. 9B and 9C, sharps container 304 further includes a sharps container cover 311 attached to the sharps container by a hinge thereby providing a means for swinging cover 311 across the top and closing sharps container 304. Sharps container 304 and cover 311 further include a means for locking the cover in place thereby sealing the open end of sharps container 304. In the preferred embodiment, the cover locking means comprises a tab 351 fabricated to fit into receiving means 371 thereby frictionally holding cover 311 over the open end of sharps container 304. Notably, all of the sharp points and cutting edges of the drug delivery system of the present invention are contained within sharps container 304 once the cover is closed. Thus, by removing the sharps container 304 from the holster, all dangerous elements of the system can be isolated and safety controlled.

A partial barrier 910 extends across a partion of the top of the cylindrical container portion of the sharps container in order to prevent used cannula from escaping from the container through the top. A passage 912 is provided through the barrier 910 into the cylindrical container portion to allow severed cannula to be deposited therein.

Referring now to FIGS. 3, 4, 5, 5A, 5B and 5C in particular, the holster and cartridge disposal device 300 is shown with gun style injection device 100 inserted into gun receptacle 302. The action of inserting injection device 100 into holster 300 occurs once an operator of the device has completed the injection and delivery of the formula in the drug cartridge installed in the injection device 100. It is subsequently desired to sever the cannula from the spent drug cartridge and to dispose of the cannula and cartridge into separate compartments within holster 300. Injection device 100 and holster 300 comprise cooperative means for performing these operations as the following description will demonstrate.

Figure 5A:
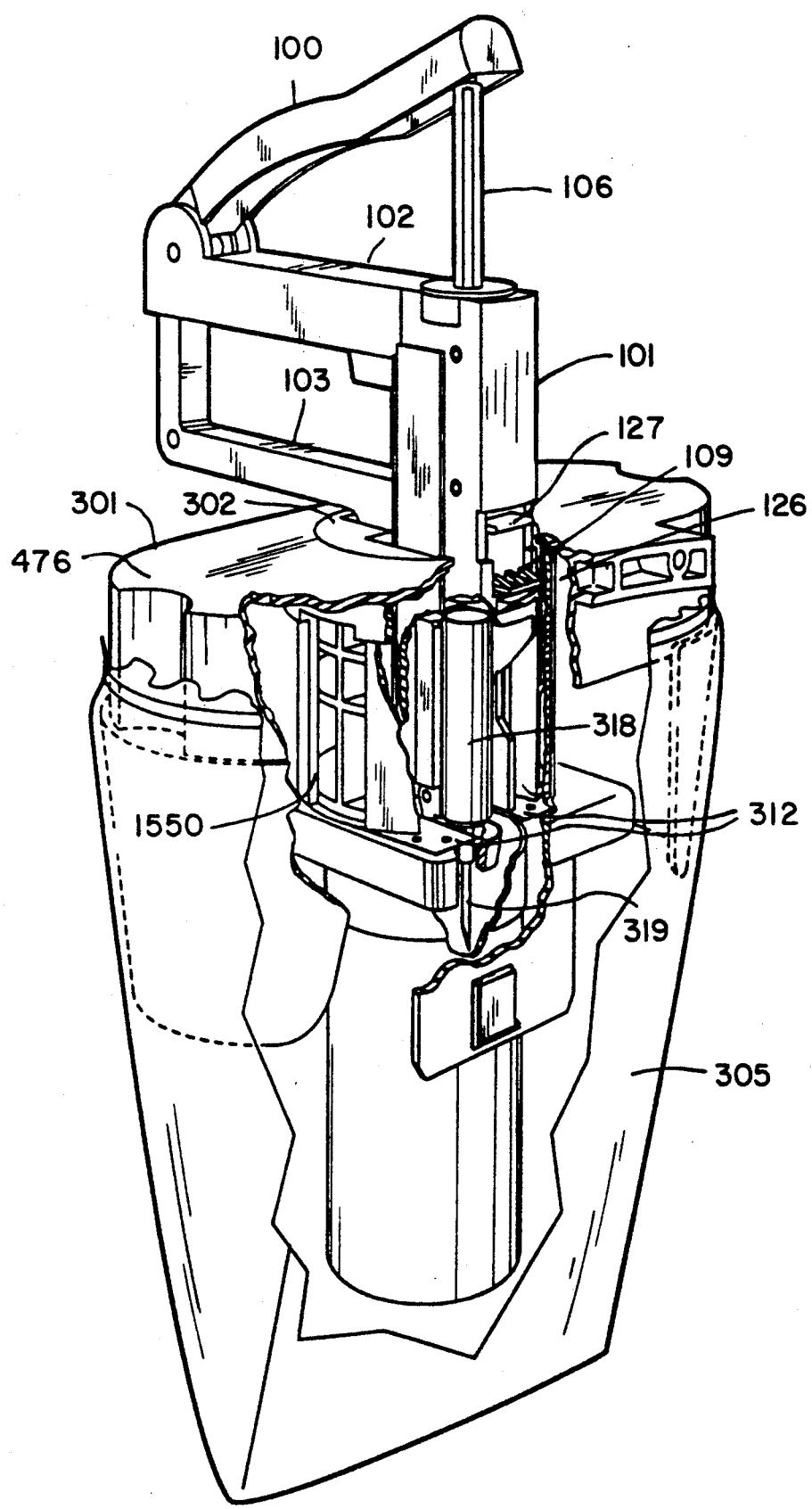
FIG. 5A is a perspective view of the combination of FIG. 5 shown partially broken away.
Figure 5B:
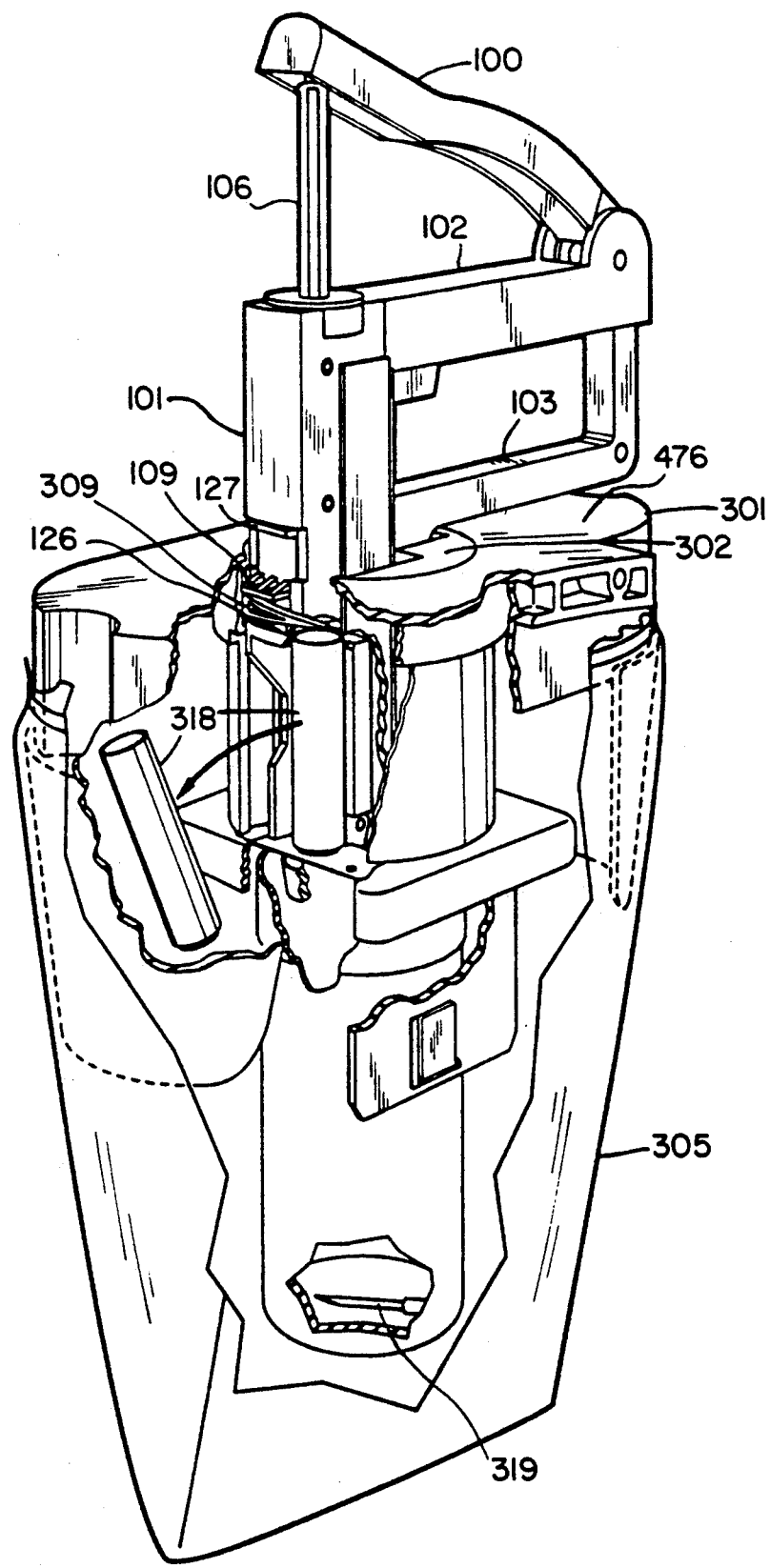
FIG. 5B is the same perspective view of the combination of FIG. 5A as shown in FIG. 5A with the gun style injection device rotated 90° from its position in FIG. 5A.

The cooperative operation of the injection device 100 and holster 300 occurs in two basic steps. First, injection device 100 is inserted into holster device 300 as shown in FIG. 3. Secondly, injection device 100 is rotated in either direction depending on the setting of the rotation direction select switch 307. This injection device rotation step is depicted in FIGS. 5A and 5B. As the injection device is rotated, two operations occur at two positions of angular rotation. In the preferred embodiment, the first angular position is 45° of rotation in either direction from the insertion position of the injection device. The second angular position in the preferred embodiment is 90° of rotation in either direction from the insertion position of the injection device. It will be apparent to those skilled in the art that the two operations described below at each angular position of rotation may occur at angular positions different from 45° and 90°.

Figure 17:
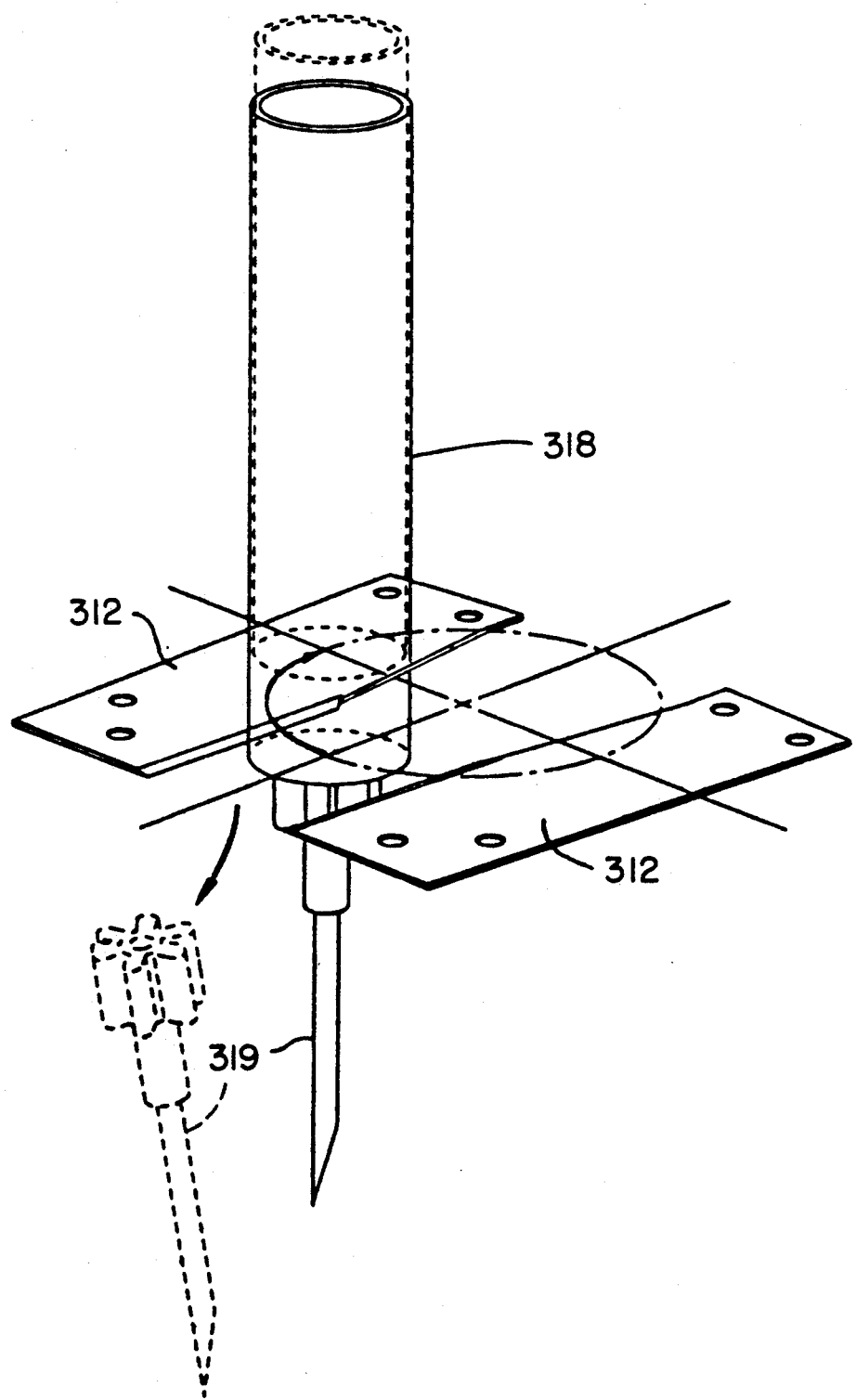
FIG. 17 shows the relationship of the cartridge and needle to the severing means of the system as the cartridge is rotated.

In the preferred embodiment during the first 45° of rotation of injection device 100 in either direction, the cannula 319 is severed from the spent drug cartridge by one of a set of blades 312 attached to the sharps container 304 which is installed within holster 300. This is shown schematically in FIG. 17 where the cartridge 318 and cannula 319 in solid lines is in the initial position while the dotted lines shows what happens when the gun and receptacle are rotated 45°. See also FIG. 4. During the second 45° of rotation of injection device 100, the ejection means of injection device 100 is activated by cooperating components coupled to holster 300. Specifically, a wedge member 309 attached to the inside surface of each of the receptacle housing halves 1540 and 1542 serves to activate the ejection means of injection device 100 thereby causing the used and severed cartridge to be forcibly ejected from injection device 100 through opening 1530 in receptacle 302 and either opening 1550 or 1552 in receptacle housing 1540 or 1542, respectively, and into cartridge disposal bag 305. Notably, the sharps container 304 and cartridge disposal bag 305 provide two separate containers for holding different portions of the spent drug cartridge. The two portions of the spent drug cartridge can therefore be disposed of separately.

Figure 4:
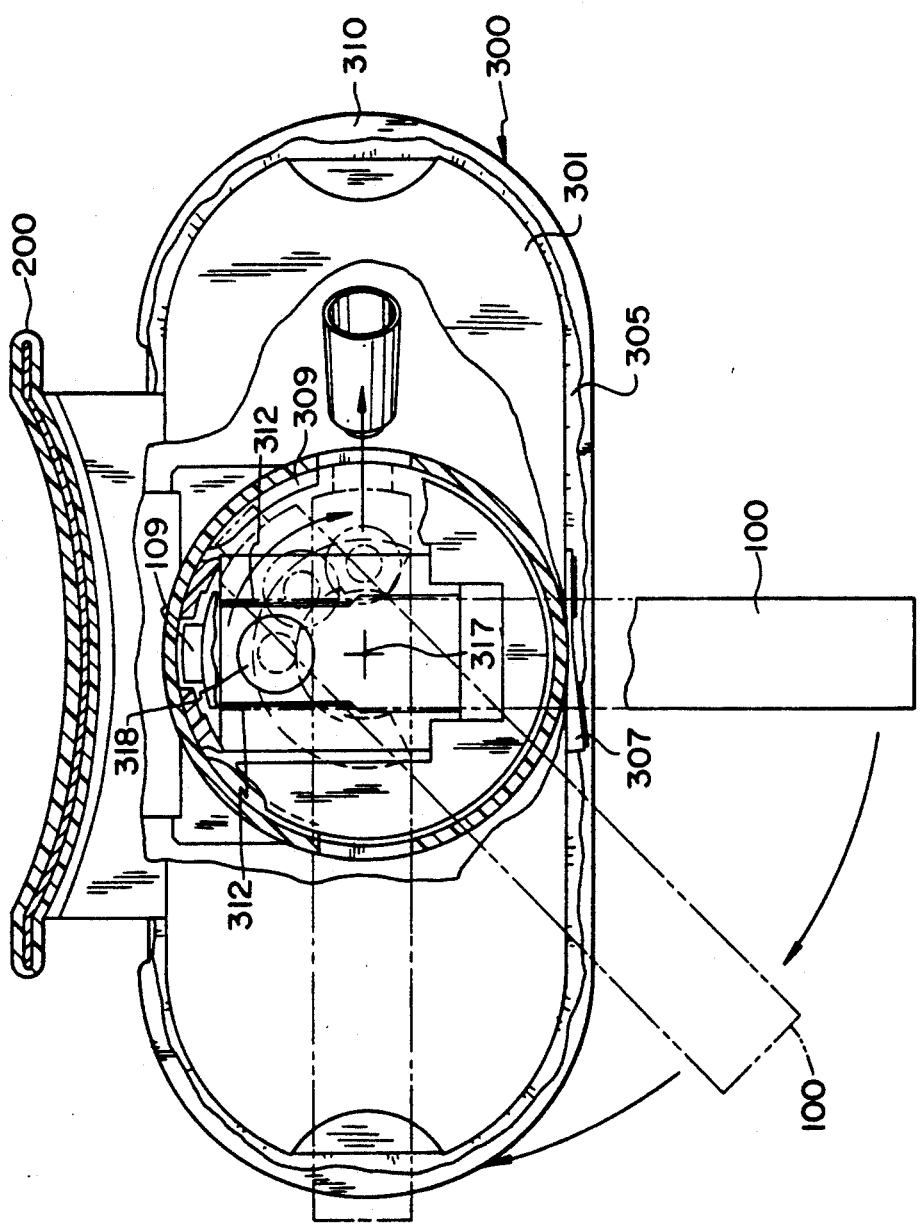
FIG. 4 is a top view of the holster showing the angular movement of the gun style injection device inserted therein (shown in phantom) and the subsequent separation of the spent drug cartridge.

Referring now to FIG. 4, a view of holster 300 from a vantage point above gun receptacle 302 is shown. An outline of injection device 100 in dash and dotted lines as inserted into the holster 300 is also shown. The center of rotation 317 of the injection device 100 is also indicated. Since the drug cartridge 318 installed within injection device 100 is slightly off center of center point 317, cartridge 318 changes position along an arcuate path when injection device 100 is rotated as shown. By virtue of this change in position of drug cartridge 318, the rotation of injection device 100 moves the cartridge 318 into one of two spaced apart cutting blades 312 depending upon direction of rotation. As the injection device 100 completes 45° of rotation, the cutting blade 312 will have severed the cannula from the body of the cartridge. By the time injection device 100 has completed 90° of rotation, the severed cartridge will have moved into a position directly above blade 312 and the severed cannula will have dropped through an opening between blades 312 and into sharps container 304. The rotation of injection device 100 thus provides a means for severing a cannula from a drug cartridge.

Referring now to FIG. 5, 5A and 5B, the operation of the cartridge ejection means and the severing of the cannula from the cartridge is illustrated. Again in FIG. 5, injection device 100 is shown inserted into gun receptacle 302 subsequent to the delivery of the dosage of drug formulation from drug cartridge 318. Ejection release means 109 and ejection support means 126 are also shown. In addition, edge 122 of ejection release means 109 is shown holding drug cartridge 318 in the operating position within injection device 100. Wedge member 309 is also shown in a position aligned with slot 123 between ejection release switch 109 and ejection support means 126.

As injection device 100 is rotated the first 45° of rotation, cartridge 318 and cannula 319 are moved into contact with cutting blade 312 as described above. As rotation continues, cannula 319 is severed from cartridge 318 and falls into sharps container 304. As rotation of injection device 100 continues for the second 45° of rotation, the leading tip of wedge member 309 begins entry into slot 123. As rotation of the injection device 100 continues, wedge member 309 separates ejection release means 109 from ejection support means 126. Ejection release means 109 is thereby forced backward and away from cartridge 318. As this wedging action continues, edge 122 of ejection release means 109 eventually ceases to make contact with cartridge 318. In so doing, edge 122 ceases to apply downward pressure on cartridge 318. With downward pressure being released from cartridge 318, spring 121 on the under side of cartridge ejection means 108 of injection device 100 is now free to forcibly push severed cartridge 318 from the chamber 110 of injection device 100. The severed drug cartridge 318 then flips out of injection device 100 and into cartridge containment bag 305. This leaves the cartridge chamber 110 of injection device 100 in the loading configuration. As injection device 100 is rotated back to its initial starting position, wedge member 309 is removed from slot 123 and ejection release switch 109 returns to the forward (cartridge lock) position. In this position, ejection release 109 is again positioned to receive and lock in a new drug cartridge. Once the injection device 100 is rotated back to the initial start position, the injection device 100 may be removed from holster 300 and thereafter loaded with a new pre-filled drug cartridge. The cycle of injecting, delivering and disposing of a new cartridge may then be repeated.

The holster may be manufactured of a plastic or metal material suitable for rugged operation and outdoor operating environments. The preferred embodiment is manufactured from a polycarbonate material of a thickness suitable to provide a durable and lightweight holster. The leg protection panel 200 and attached holster 300 are designed with belt loops and a leg strap on the back side of leg protection panel 200 in order to provide a means for hanging the holster form the waist belt of a user of the system. In this way, the drug delivery system disclosed herein is a light-weight, highly portable and efficient device.

Figure 6A:
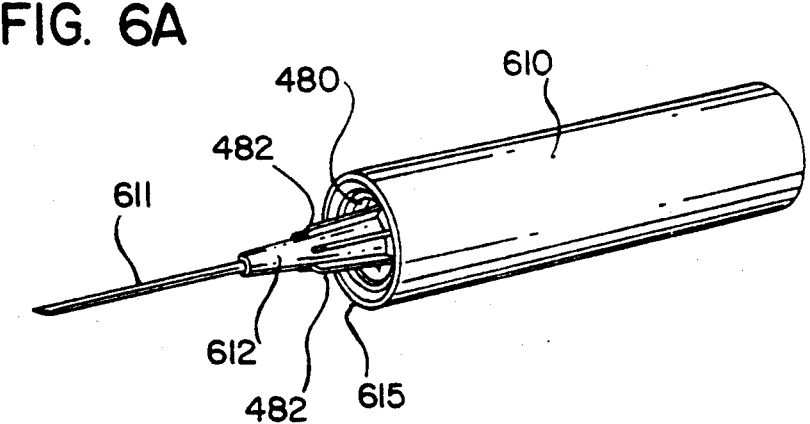
FIGS. 6A–C depict an improvement to the cartridge and ejection plate of the injection device.
Figure 6B:
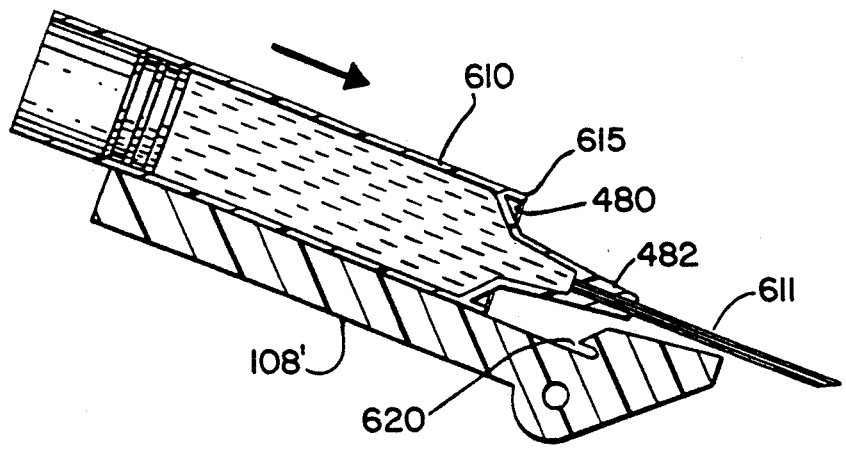
Figure 6C:
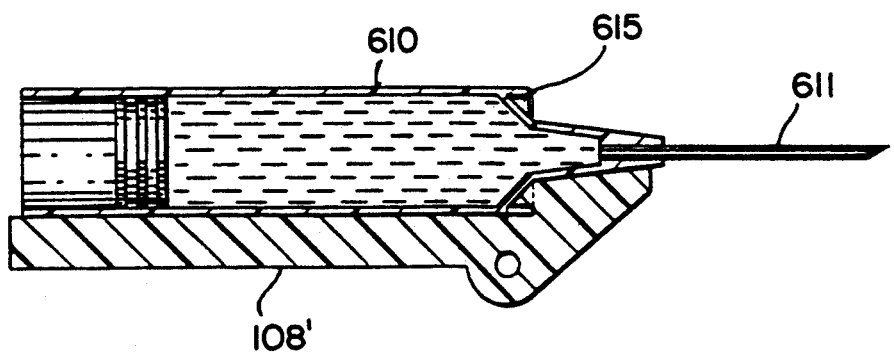

The cartridge design itself is improved in the present invention in order to increase the performance of the gun style injection device and the holster cannula severing mechanism. Referring to FIG. 6a, an improvement to the cartridge and a corresponding modification to the ejection plate of the gun style injection device is illustrated. As shown, a ridge 615 is added to the cartridge cylinder 610 at the end joining the cannula 611. Ridge 615 is formed by extending the cylindrical surface of the cylinder 610 at the cannula end thereby creating an annular recessed region 480 in which cannula 611 is coupled to an end of cylinder 610 by cannula support means 612. Cannula support means 612 includes longitudinal ribs 482 for positioning and supporting cannula 611. Ridge 615 is adapted to engage an indentation 620 in the injection device ejection means 108 thereby locking the cannula end of the cartridge 610 solidly in place for more efficient cutting by the blade 312 of the holster severing mechanism. As the improved cartridge is loaded into the injection device 100 as shown in FIG. 6B, ridge 615 engages indentation 620. When the cartridge 610 is then depressed into the operating position as shown in FIG. 6C, the cartridge 610 is locked into place by the cooperation of ridge 615 and indentation 620 at the cannula end of the cartridge. At the other end, the cartridge is locked into place by the ejection release means 109. Since the cartridge is firmly locked into place in the injection device, the cannula severing operation performed by the holster 300 is more efficient. There is less slippage of the cartridge as the cartridge is forced into blade 312 as described above. Further, the locking of the cartridge using the ridge improvement serves to more accurately position and align the cartridge for cutting in a predictable location along cannula support means 612. The ridge 615 and indentation 620 improvement also minimizes a gun jamming problem experienced in prior art cartridge devices. In the manufacture of plastic cartridges, sometimes residual material is left behind from the molding process around the circumference of the rear end (i.e. end opposite of cannula end) of the cartridge. The residual material can sometimes act as a catch when the ejection release 109 is activated to eject a cartridge from the gun. If the rear end of the cartridge is caught by the ejection release 109, the cartridge is pulled rearward clear of cartridge guide 107 causing the severed end of a cartridge to flip out of chamber 110 before the rear end of the cartridge. This action may cause the gun-style injection device 100 to jam. Ridge 615 in cooperation with indentation 620 serves to hold the severed end of a cartridge solidly in chamber 110 thereby minimizing the potential for a cartridge to jam the gun 100.

An additional improvement to the cartridge of the present invention is depicted in FIG. 7A. As shown in FIG. 7A, the ribs of cannula support means 615 are modified to provide a wedging surface 715 adapted to properly align and position the holster severing blade 720 for more accurate cutting. Wedging surface 715 is formed by varying the cut of each rib to create an inclined edge as shown in FIGS. 7A–D. As illustrated in the sequence of FIGS. 7B–D, the wedge shape 717 of the edge of holster blade 720 cooperates with the cartridge wedging surface 715 to urge the cartridge 710 slightly upward as shown by arrow 716 in FIG. 7C as the cartridge 710 is forced into blade 720 in the manner described above. This slight movement of cartridge 710 serves to properly align the cartridge relative to blade 720 just prior to the severing of the cannula depicted in FIG. 7D.

Figure 8A:
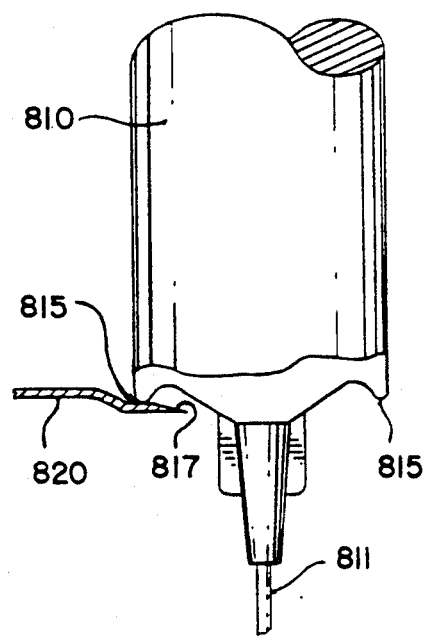
FIGS. 8A–C illustrate an alternative improvement to the cartridge and holster severing blade.
Figure 8B:
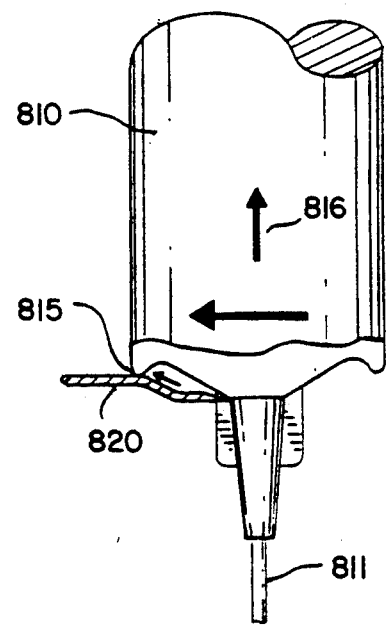
Figure 8C:
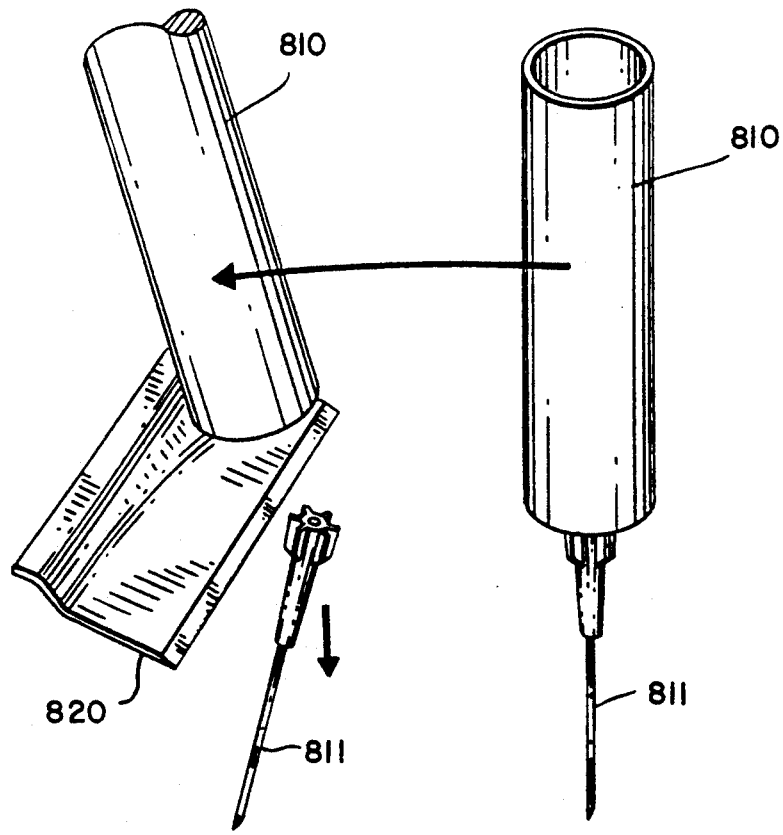

Referring now to FIGS. 8A–C, an alternative embodiment of the improvement to the cartridge of the present invention is illustrated. In this alternative embodiment, an improvement to the cartridge and a corresponding modification to the severing blade of the holster device is made. As shown, a ridge 815 is added to the cartridge cylinder 810 at the end joining the cannula 811. Ridge 815 may be formulated in a manner similar to the ridge 615 described above and illustrated in FIGS. 6A–C. Referring still to FIG. 8A, a wedging surface 817 is formed on blade 820. A method for forming a blade in the shape shown in FIGS. 8A–C will be apparent to those skilled in the art. This blade wedging surface cooperates with ridge 815 to urge cartridge 810 in an upward direction as shown by arrow 816 as cartridge 810 is forced into blade 820 during the cannula severing operation described above. This slight upward movement of cartridge 810 serves to properly align the cartridge 810 relative to blade 820 just prior to the severing of the cannula depicted in FIG. 8C.

Two additional improvements to the injection device are also described herein. First, an improvement to the injection device provides a means for adjusting the dosage of drug delivered by the system. A second improvement to the ejection plate of the injection device provides a means for allowing cartridge rotation in one direction only, thereby facilitating removal of the cannula cap and proper positioning of the angled cannula tip.

Figure 10:
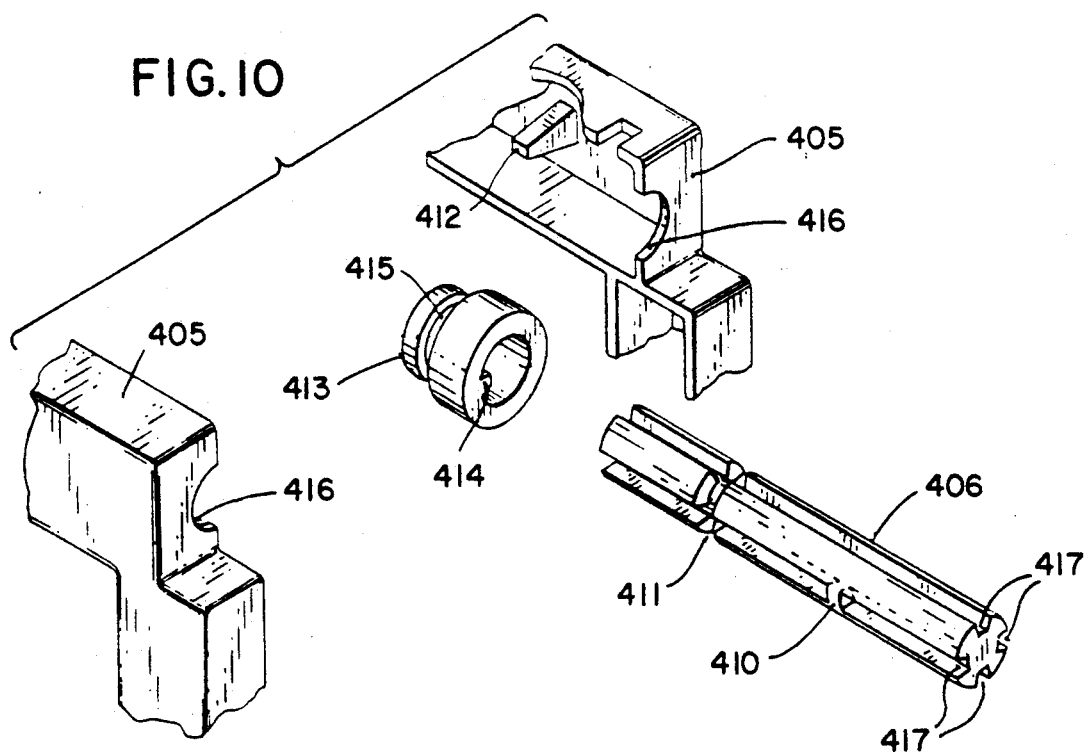
FIG. 10 illustrates an improvement to the injection device providing a means for adjusting the dosage of drug delivered by the system shown in exploded view.

Referring to FIG. 10, a further improvement to the injection device 100 provides a means for adjusting the dosage of drug delivered by the present invention. A collar 415 of dosing knob 413 is captured by two notches 416 in each half 405 of the proximal or handle end of injection device barrel housing 101 as the barrel 101 is assembled. Dosing knob 413 is free to rotate within barrel 101. Dosing knob 413 is formed with a cylindrical cavity in which push rod 406 may be slideably inserted. A set of longitudinal grooves 417 in push rod 406 cooperate with a tooth 414 positioned in the interior cavity of dosing knob 413. A lateral groove 411 is cut at a particular location in push rod 406 such that tooth 414 is positioned in lateral groove 411 when push rod 406 is in the relaxed position. With tooth 414 positioned in lateral groove 411, dosing knob 413 is free to rotate 360° around push rod 406. By allowing this rotation of dosing knob 413, the user of the injection device is able to select one of four different dosing positions corresponding to the four longitudinal grooves 417 in push rod 406. At each of the four positions, tooth 414 is aligned with one of the longitudinal grooves 417. Once tooth 414 is aligned with one of the longitudinal grooves 417, push rod 406 becomes free to travel into the barrel housing 101 through dosing knob 413 until tooth 414 makes contact with a stop member 410 positioned within and perpendicular to longitudinal groove 417. The push rod 406 travel distance between lateral groove 411 and stop member 410 corresponds to the amount of drug forced out of the cartridge by the push rod 406. In each of the four longitudinal grooves 417, a stop member 410 is positioned at a different distance from lateral groove 411. Thus, by rotating dosing knob 413 located on the barrel housing 101 and selecting one of the four different longitudinal grooves 417, a user of the injection device may select one of four different dosage levels delivered by the injection device.

Figure 13:
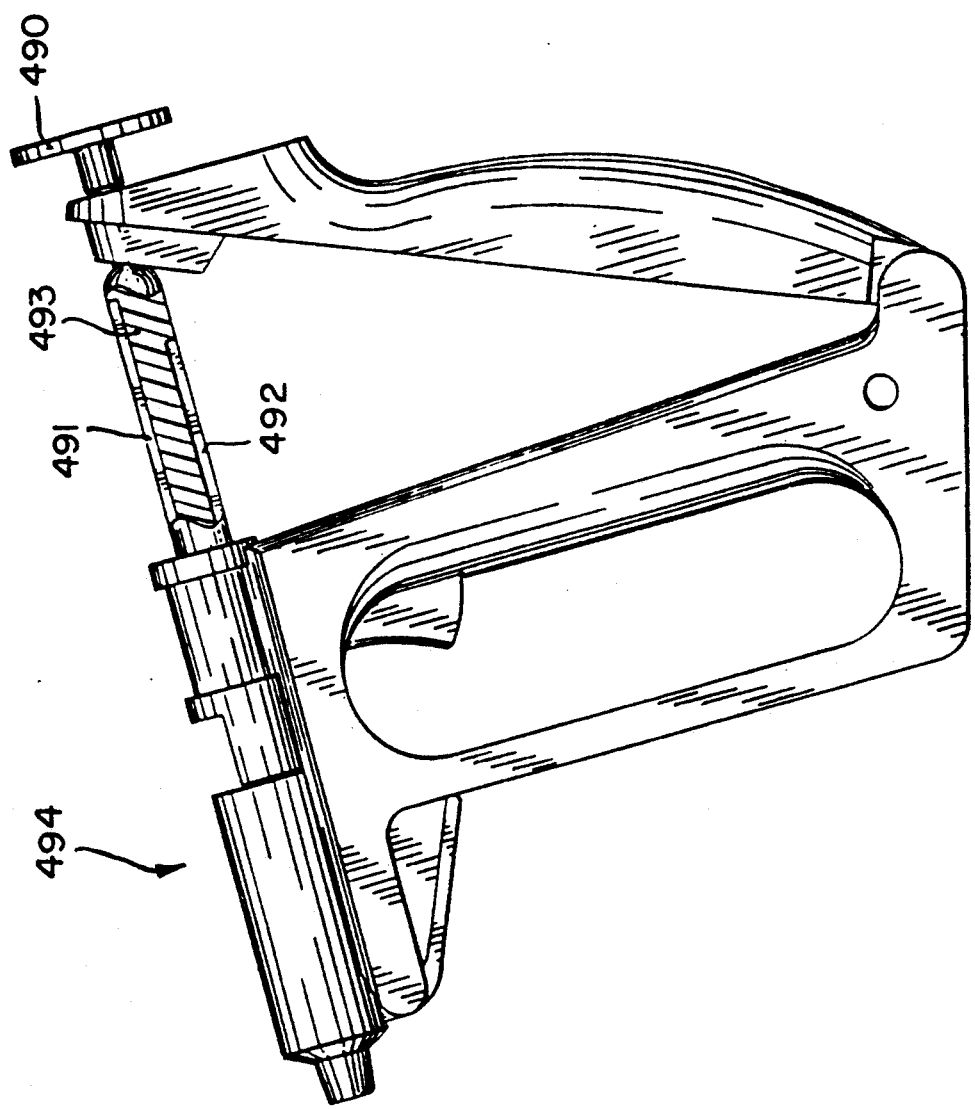
FIG. 13 illustrates an alternative embodiment of the gun style injection device with a means for adjusting the dosage of drug positioned on the back end of the push rod instead of positioned on the barrel housing.

In an alternative embodiment, an injection device designated 494, as illustrated in FIG. 13, provides a dosing means 490 coupled to a push rod 493. The dosing means is used to rotate the push rod thereby enabling the use of one of two channels 491 or 492 cut into the push rod. The channels are of two different lengths thereby limiting the travel of the push rod to two different positions. These two positions correspond to two different drug dosages delivered by the gun.

Figure 11A:
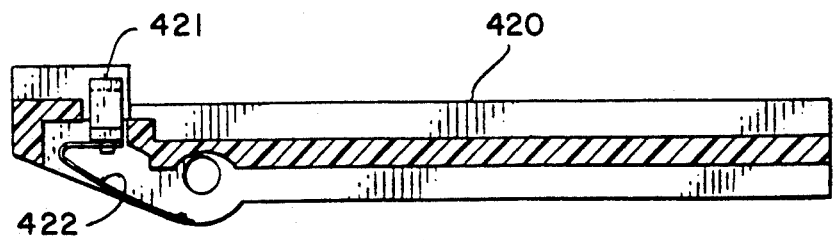
FIGS. 11A and 11B illustrate a further improvement to the ejection plate of the injection device providing a means allowing cartridge rotation in one direction, but limiting rotation in the other direction.
Figure 11B:
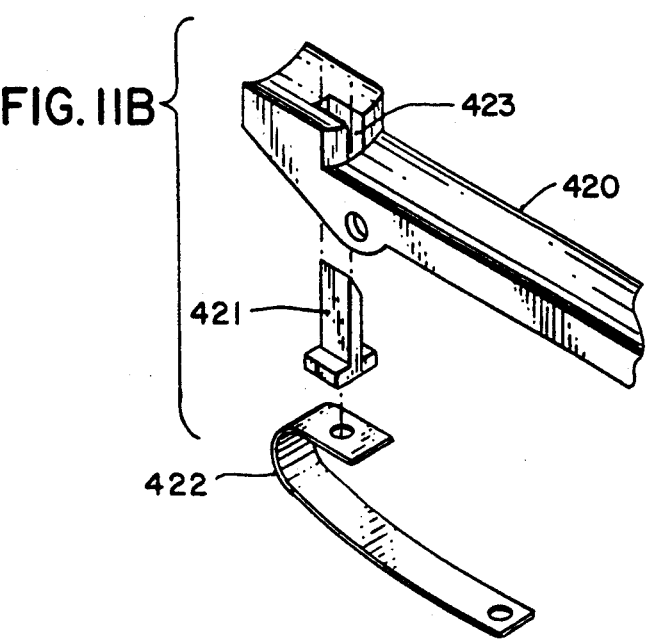

Referring now to FIGS. 11A and 11B, an improvement to the ejection plate 420 of injection device 100 provides a ratchet means for allowing cartridge rotation in one direction, but limiting rotation in the other direction. By limiting rotation in one direction, the cartridge becomes securely fixed in position thereby facilitating removal of a cap covering the cannula. By allowing rotation in the opposite direction, the cartridge becomes rotatable for proper alignment of the angled tip of the cannula.

Referring again to FIGS. 11A and 11B, and FIG. 14, ejection means 420 is shown. An angled tooth 421 is shown extending through an opening 423 in the ejection means 420. Spring 422 urges tooth 421 upward into opening 423, but allows tooth 421 to be depressed downward to a point where the upper edge of tooth 421 is flush with the upper surface of ejection means 420. Tooth 421 is positioned in ejection means 420 at a location corresponding to the position of the longitudinal ribs 482 of the cannula support means 612 of a cartridge resting on the upper surface of ejection means 420. The longitudinal ribs 482 are shown in FIG. 6A. Tooth 421 is angled to a point edge designed to fit between each of the longitudinal ribs 482 of the cannula support means 612. As the cartridge is rotated in one direction, each rib strikes the angled surface of tooth 421 thereby forcing tooth 421 downward by the wedge action of the angled surface. As each rib rotates past tooth 421, spring 422 causes tooth 421 to return to its full upward position between ribs until the next rib causes the downward force on the angled surface. Thus, the angled surface of tooth 421 allows rotation of the cartridge. However, rotation in the opposite direction is prevented, since an angled surface is present on only one side of tooth 421. Thus, a rib rotating in the opposite direction cannot cause downward pressure on tooth 421. Tooth 421 therefore remains in place thereby preventing opposite rotation of the cartridge.

Thus, a belt worn, drug delivery system used for delivering a dosage of formulation from a pre-filled drug cartridge and thereafter severing and disposing of used drug cartridges is disclosed.

Although this invention has been shown in relation to particular embodiments, it should not be considered so limited. Rather, it is limited only by the appended claims.

What is claimed is:

1. An injection device for administering a formulation from a pre-filled cylindrical cartridge with attached cannula, said injection device comprising:
   a barrel having a cylindrical bore and a chamber adapted for receiving and positioning a cartridge coaxial with said bore;
   a push rod slideably disposed within and coaxial to said bore, said push rod for pushing the contents of the cartridge through the cannula;
   an ejection plate coupled to said barrel within said chamber and a spring coupled to said barrel and said ejection plate, said ejection plate moveable between a cartridge loading position wherein one end of said ejection plate is extended out of said chamber and an operating position wherein both ends of said ejection plate are positioned within said chamber, said spring biasing said ejection plate to said cartridge loading position; and
   an ejection release means coupled to said barrel for locking and releasing said ejection plate, said ejection release means operating between a cartridge lock position wherein a portion of said ejection release means holds said cartridge in the operating position within said chamber such that a cartridge resting on said ejection plate is positioned coaxial with the bore of said barrel, and a cartridge release position wherein said ejection release means is moved away from contact with a cartridge loaded in said chamber, whereby said ejection plate forcibly removes a spent cartridge from said barrel in response to said spring after said cannula has been removed from said cartridge.

2. The injection device as claimed in claim 1 wherein said injection device is a gun-style device with a handle and a trigger, said handle being coupled to said barrel and said trigger being coupled to said handle.

3. The injection device as claimed in claim 2 wherein said handle comprises a hinged lever hinged at one end of said handle and coupled at the other end to said push rod, said hinged lever moving said push rod within said cylindrical bore of said barrel between an extended position and a relaxed position, said injection device further including a spring coupled to said handle for urging said hinged lever and said push rod to said relaxed position.

4. The injection device as claimed in claim 2 including a trigger tab coupled to said trigger for preventing said push rod from being moved within the bore of said barrel, said trigger operating between a relaxed position wherein said push rod is prevented from moving within said bore by contact with said trigger tab and a release position wherein said trigger tab is removed from contact with said push rod by operating said trigger, said injection device further including a spring coupled to said trigger for urging said trigger to the relaxed position.

5. The injection device of claim 1 wherein said device further comprises dosing means for selecting one of at least two portions of the contents of the cartridge to be delivered when administering the formulation.

6. The device of claim 5 wherein said dosing means comprises a plurality of spaced apart longitudinal grooves of different lengths in said push rod; means located within said cylindrical bore to travel along a selected longitudinal groove and engage an end thereof when said push rod moves into said bore; and means for selecting one of said grooves.

7. The device of claim 6 wherein said selection means comprises a knob coupled to said push rod whereby said push rod can be rotated.

8. The device of claim 6 wherein said means located within said bore is a tooth connected to a rotatable knob coupled to said barrel and said push rod comprises a circumferential groove for allowing said tooth to pass there along when said knob is rotated.

* * * * *